US011191733B2

(12) United States Patent
Okada et al.

(10) Patent No.: US 11,191,733 B2
(45) Date of Patent: Dec. 7, 2021

(54) DRUG DELIVERY PARTICLE AND METHOD FOR PRODUCING THE SAME

(71) Applicant: National Center of Neurology and Psychiatry, Tokyo (JP)

(72) Inventors: Takashi Okada, Tokyo (JP); Shin'ichi Takeda, Tokyo (JP); Hiromi Kinoh, Tokyo (JP)

(73) Assignee: NATIONAL CENTER OF NEUROLOGY AND PSYCHIATRY, Tokyo (JP)

(*) Notice: Subject to any disclaimer, the term of this patent is extended or adjusted under 35 U.S.C. 154(b) by 0 days.

(21) Appl. No.: 15/445,157

(22) Filed: Feb. 28, 2017

(65) Prior Publication Data
US 2017/0172936 A1 Jun. 22, 2017

Related U.S. Application Data

(63) Continuation of application No. 14/112,317, filed as application No. PCT/JP2012/060229 on Apr. 16, 2012, now Pat. No. 9,610,354.

(30) Foreign Application Priority Data

Apr. 18, 2011 (JP) .............................. JP2011-092252

(51) Int. Cl.
| | | |
|---|---|---|
| A61K 35/76 | (2015.01) | |
| A61K 48/00 | (2006.01) | |
| A61K 38/17 | (2006.01) | |
| A61K 9/51 | (2006.01) | |
| A61K 31/7088 | (2006.01) | |
| A61K 31/713 | (2006.01) | |
| A61K 9/14 | (2006.01) | |
| A61K 47/42 | (2017.01) | |
| C12N 5/00 | (2006.01) | |
| C12N 7/00 | (2006.01) | |
| C12N 15/113 | (2010.01) | |
| A61K 47/26 | (2006.01) | |

(52) U.S. Cl.
CPC .............. *A61K 9/5184* (2013.01); *A61K 9/14* (2013.01); *A61K 31/7088* (2013.01); *A61K 31/713* (2013.01); *A61K 47/42* (2013.01); *A61K 48/0008* (2013.01); *A61K 48/0091* (2013.01); *C12N 5/00* (2013.01); *C12N 7/00* (2013.01); *C12N 15/113* (2013.01); *A61K 47/26* (2013.01); *C12N 2310/14* (2013.01); *C12N 2320/32* (2013.01); *C12N 2510/02* (2013.01); *C12N 2710/10042* (2013.01); *C12N 2750/00042* (2013.01); *C12N 2750/00051* (2013.01); *C12N 2750/14142* (2013.01)

(58) Field of Classification Search
CPC .............. A61K 31/7088; A61K 31/713; A61K 47/26; A61K 47/42; A61K 9/14; A61K 9/5184; A61K 48/0008; A61K 48/0091; C12N 2710/10042; C12N 2750/14142; C12N 15/113; C12N 2310/14; C12N 2320/32; C12N 2510/02; C12N 2750/00042; C12N 2750/00051; C12N 5/00; C12N 7/00; A61P 43/00

USPC ....... 424/400, 490, 491, 499; 514/1.1, 44 R; 435/235.1, 456, 455, 489

See application file for complete search history.

(56) References Cited

U.S. PATENT DOCUMENTS

| | | | |
|---|---|---|---|
| 5,292,524 A | 3/1994 | Male et al. | |
| 5,863,541 A | 1/1999 | Samulski et al. | |
| 6,033,895 A | 3/2000 | Garger et al. | |
| 7,125,705 B2* | 10/2006 | Colosi ................. | C07K 14/005 435/235.1 |
| 2006/0165726 A1* | 7/2006 | Kuroda ................ | A61K 9/5068 424/227.1 |

FOREIGN PATENT DOCUMENTS

| | | |
|---|---|---|
| EP | 1 491 215 A1 | 12/2004 |
| JP | 2001169777 A | 6/2001 |
| JP | 2001520050 A | 10/2001 |
| JP | 2003024092 A | 1/2003 |
| JP | 2004503216 A | 2/2004 |
| JP | 2005-314476 | 4/2004 |
| JP | 2008-029249 A | 2/2008 |
| JP | 2010-077091 A | 4/2010 |
| JP | 2011509661 A | 3/2011 |

(Continued)

OTHER PUBLICATIONS

Okada, T. and Takeda S., *Advances in Molecular Therapy Research on Dystrophin-Deficient Muscular Dystrophy*, World Scientific, NJ, 2010, 5(1), pp. 113-123.

Extended European Search Report in corresponding European Application No. 12773753.4, dated Aug. 27, 2014, 5 pages.

Office Action in corresponding U.S. Application No. 14/112,317, dated Jan. 15, 2016, 9 pages.

Office Action in corresponding U.S. Application No. 14/112,317, dated Jul. 12, 2016, 8 pages.

(Continued)

*Primary Examiner* — Janet L Epps -Smith
(74) *Attorney, Agent, or Firm* — Crowell & Moring LLP

(57) ABSTRACT

An object of the present invention is to develop and provide a method for conveniently introducing a nucleic acid, a peptide, and/or a low-molecular-weight compound into an empty capsid with viral early infection activities kept. The present invention provides a method for producing a drug delivery particle, comprising the steps of: mixing an empty capsid or an empty particle with a drug including a nucleic acid, a peptide, and/or a low-molecular-weight compound in a solution comprising 0.1 to 20% of a surfactant; and keeping the obtained mixed solution at −5 to 50° C. to introduce the drug into the empty capsid or the empty particle.

4 Claims, 6 Drawing Sheets
Specification includes a Sequence Listing.

(56) References Cited

FOREIGN PATENT DOCUMENTS

| WO | WO 95/34670 | 12/1995 | | |
|---|---|---|---|---|
| WO | WO 96/40270 A1 | 12/1996 | | |
| WO | WO 99/20778 | 4/1999 | | |
| WO | WO 01/25464 A1 | 4/2001 | | |
| WO | WO 01/83797 A2 | 11/2001 | | |
| WO | WO 01/90342 A2 | 11/2001 | | |
| WO | WO-0183797 A2 * | 11/2001 | ........... | C07K 14/005 |
| WO | WO 03/046142 A2 | 6/2003 | | |
| WO | WO 03/082344 A1 | 10/2003 | | |
| WO | WO 2006/078279 A2 | 7/2006 | | |
| WO | WO 2007/116808 A1 | 10/2007 | | |
| WO | WO 2009/076778 A1 | 6/2009 | | |
| WO | WO 2010/129021 A1 | 11/2010 | | |
| WO | WO 2010/0148143 A1 | 12/2010 | | |

OTHER PUBLICATIONS

Partial European Search Report in corresponding European Application No. 17161879.6, dated Jul. 7, 2017, 8 pages.
Office Action, and English language translation thereof, in corresponding Chinese Application No. 2016-165350, dated Sep. 12, 2017, 8 pages.
Extended European Search Report in corresponding European Application No. 17161879.6, dated Nov. 6, 2017, 8 pages.
Reporting Letter received from the Japanese associate enclosing Japanese Office Action dated Mar. 5, 2019 and cited references.
Office Action dated Mar. 5, 2019 received in Japanese Patent Application No. 2018-090289.
Office Action, and English language translation thereof, in corresponding Japanese Application No. 2016-165350, dated Sep. 12, 2017, 8 pages.

* cited by examiner

Fig. 5
A 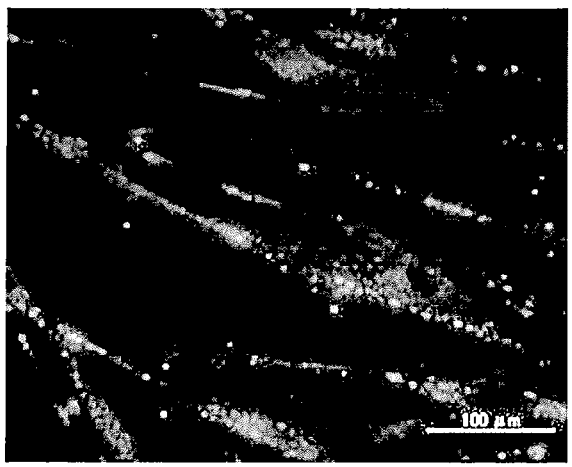
B 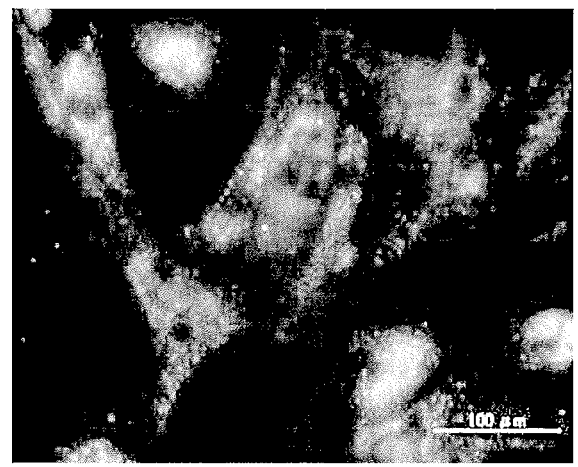

DRUG DELIVERY PARTICLE AND METHOD FOR PRODUCING THE SAME

This application is a continuation of and claims priority to U.S. application Ser. No. 14/112,317 filed Oct. 17, 2013, International Application No. PCT/JP2012/060229 filed Apr. 16, 2012, and Japanese Application No. 2011-092252 filed Apr. 18, 2011, the entire contents of each are incorporated herein by reference.

TECHNICAL FIELD

The present invention relates to a drug delivery particle, a method for producing the same, and a drug composition comprising the drug delivery particle as an active ingredient.

BACKGROUND ART

Various gene transfer techniques have been developed in order to introduce genes of interest to cells, tissues, or individuals and express the genes. One of such techniques is viral vectors based on the infectious or replicating ability of viruses. Various vectors derived from retrovirus, adenovirus, adeno-associated virus, and the like are known. Among them, adeno-associated virus vectors have been expected as gene transfer carriers useful in gene therapy in recent years.

The adeno-associated virus (AAV; hereinafter, referred to as "AAV" in the present specification) is a non-pathogenic virus that belongs to the family Parvoviridae. This virus lacks self-renewal ability and therefore cannot autonomously grow. Since its growth requires coinfection by adenovirus or herpesvirus, AAV is low infective. AAV also has the property of low immunogenicity in hosts. Owing to such features, AAV is advantageously highly safe as a gene transfer carrier. In addition, AAV is capable of infecting various cells because of its wide host range. Moreover, vectors derived from each of AAV serotypes 1 to 9 have also been developed (Non Patent Literature 1) and therefore permit gene expression in particular cells (e.g., nerve cells, muscle cells, and hepatic cells), tissues, and organs by the application of the specificity of the target cells to be infected for each serotype.

All of the conventional viral vectors including AAV vectors, however, have presented various problems against recipient individuals, such as in vivo transient gene expression, possible contamination by wild-type viruses, time required for gene expression and manifestation of the action thereof, impossible incorporation of large genes, and the need of a mechanism for controlling expression when side reaction appears.

In order to solve these problems, Samulski et al. have proposed expressing capsids with AAV capsid expression plasmids and using them as drug delivery carriers (Non Patent Literature 2). Vacant capsids containing no viral genome therein, i.e., empty capsids, have viral early infection activities such as specific recognition of target cells, adsorption, penetration, and uncoating, but lack a viral growth activity because of having no virus-derived gene. Thus, the empty capsids can serve as ideal drug delivery system (DDS) carriers that have both the target cell-specific delivery of drugs and safety in recipient individuals. Hence, the technique of introducing drugs of interest to the inside of the capsids is very important for using the empty capsids as DDS carriers.

Samulski et al. have reported an introduction method which involves temporarily denaturing an empty capsid using urea, heat, or pH conditions to allow the capsid to take up a drug, and then reconstituting the resulting capsid (Non Patent Literature 2). Upon action of a denaturant such as urea, however, the capsid disadvantageously loses its early infection activities and is thus no longer able to function as a delivery carrier. After all, the technique of introducing drugs as substances to be delivered into empty capsids with the early infection activities of the capsids kept has not yet been established even though 7 or more years have already passed from the proposal. For example, Patent Literature 1 suggests the usefulness of empty AAV particles as delivery carriers, but makes no mention about specific examples of empty capsids used as delivery carriers. Hence, those skilled in the art have shared a common understanding that the technique proposed by Samulski is impossible to realize.

CITATION LIST

Patent Literature

Patent Literature 1: Japanese Patent Application No. 2005-314476

Non Patent Literature

Non Patent Literature 1: Okada T. and Takeda S., Gene therapy for Duchenne muscular dystrophy in A Guide to Human Gene Therapy (ed. by Roland W. Herzog and Sergei Zolotukhin), World Scientific, NJ. 2010, 5 (1), pp 113-123.

Non Patent Literature 2: Samulski, et al., 1995, Appl. No.: 08/472; 594

SUMMARY OF INVENTION

Technical Problem

An object of the present invention is to solve the problems described above and to develop and provide a method for introducing a nucleic acid, a peptide, and/or a low-molecular-weight compound into an empty capsid with viral early infection activities kept.

Another object of the present invention is to provide a drug delivery particle that is produced by the method and can specifically deliver the drug of interest into a target cell.

A further object of the present invention is to develop and provide a method for enhancing the production efficiency, in a host cell, of an AAV-derived empty capsid for use in the method described above, and a method for purifying an empty viral particle.

Solution to Problem

As a result of conducting diligent studies, the present inventors have successfully introduced an arbitrary nucleic acid, peptide, and/or low-molecular-weight compound to the inside of an empty capsid with viral early infection activities kept by a convenient and efficient method. The present inventors have also confirmed that this drug-containing capsid can be treated for target cells to thereby effectively introduce the drug incorporated in the capsid into the cell. The present inventors have further developed a method for increasing the amount of an empty capsid produced in a host cell, and a method for purifying an empty capsid. The present invention is based on these findings and results and provides the followings:

(1) A method for producing a drug delivery particle comprising a capsid or an enveloped particle comprising a drug, comprising the steps of: (a) mixing an empty capsid or an empty particle with the drug in a solution comprising 0.1 to 20% of a surfactant; and (b) keeping the mixed solution after the mixing step at −5 to 50° C. to introduce the drug into the empty capsid or the empty particle.

(2) The production method according to (1), wherein the introduction step comprises keeping the mixed solution for 5 minutes to 120 minutes.

(3) The production method according to (1) or (2), further comprising the step of (c) removing the surfactant in the solution after the introduction step.

(4) The production method according to any of (1) to (3), wherein the surfactant is one or more surfactant(s) selected from the group consisting of Triton X-100, Triton X-114, NP-40, Brij-35, Brij-58, Tween-20, Tween-80, octyl-β-glucoside, OTG, SDS, CHAPS, CHAPSO, and a copolymer of PEG and PPG.

(5) The production method according to any of (1) to (4), wherein the drug is a nucleic acid, a peptide, and/or a low-molecular-weight compound.

(6) The production method according to any of (1) to (5), wherein the nucleic acid is one or more nucleic acid(s) selected from the group consisting of a functional nucleic acid, an mRNA, an mRNA fragment, and a vector comprising an arbitrary gene or a fragment thereof.

(7) The production method according to (6), wherein the functional nucleic acid is one or more nucleic acid(s) selected from the group consisting of an siRNA, an miRNA, an shRNA, a nucleic acid aptamer, an antisense DNA, a U1 adaptor, a ribozyme, a molecular beacon, and a riboswitch.

(8) The production method according to (6), wherein the vector is selected from the group consisting of a plasmid, a cosmid, and an artificial chromosome.

(9) The production method according to any of (1) to (8), wherein the empty capsid or the empty particle is modified.

(10) The production method according to any of (1) to (9), wherein the empty capsid or the empty particle has an early infection activity to a particular cell.

(11) The production method according to any of (1) to (10), wherein the empty capsid is derived from adenovirus or adeno-associated virus.

(12) A drug delivery particle comprising a drug in a capsid or an enveloped particle, wherein the drug is an exogenous nucleic acid free from genes of a virus itself from which the capsid or the enveloped particle is derived, a peptide, and/or a low-molecular-weight compound.

(13) The drug delivery particle according to (12), wherein the exogenous nucleic acid is one or more nucleic acid(s) selected from the group consisting of a functional nucleic acid, an mRNA, an mRNA fragment, and a vector comprising an arbitrary gene or a fragment thereof.

(14) The drug delivery particle according to (13), wherein the functional nucleic acid is one or more nucleic acid(s) selected from the group consisting of an siRNA, an miRNA, an shRNA, a nucleic acid aptamer, an antisense DNA, a U1 adaptor, a ribozyme, a molecular beacon, and a riboswitch.

(15) The drug delivery particle according to (13), wherein the vector is selected from the group consisting of a plasmid, a cosmid, and an artificial chromosome.

(16) The drug delivery particle according to any of (12) to (15), wherein the capsid or the enveloped particle is modified.

(17) The drug delivery particle according to any of (11) to (16), wherein the capsid is derived from adenovirus or adeno-associated virus.

(18) The drug delivery particle according to any of (11) to (17), wherein the capsid or the enveloped particle has an early infection activity to a particular cell.

(19) A drug composition comprising at least one drug delivery particle obtained by a production method according to any of (1) to (11) and/or at least one drug delivery particle according to any of (12) to (18) as an active ingredient.

(20) The drug composition according to (19), wherein the drug composition is intended for the prevention or treatment of disease or disease damage.

(21) A method for purifying an empty capsid or an enveloped particle, or a virion, comprising the step of heating a culture solution of a host cell and/or an extract of the host cell that has produced the empty capsid or the enveloped particle, or the virion, wherein the heating time is 10 minutes to 90 minutes in the case of a heating temperature of 45° C. or higher and lower than 55° C., or the heating time is 3 minutes to 30 minutes in the case of a heating temperature of 55° C. or higher and 60° C. or lower.

(22) A method for producing a cell line having the enhanced ability to produce adeno-associated virus, comprising the step of introducing an E1A gene region, an E1B19 gene, an E2A gene region, an E4orf6 gene, and a VA RNA-encoding gene derived from adenovirus to a HEK293 cell line.

(23) The production method according to (22), further comprising the step of selecting a cell line stably expressing all of the introduced genes.

(24) The production method according to (22) or (23), further comprising the steps of: introducing a human-derived Bcl-$x_L$ gene to the cell line; and selecting a cell line stably expressing the introduced Bcl-$x_L$ gene.

The present specification encompasses the contents described in the specification and/or drawings of Japanese Patent Application No. 2011-092252 on which the priority of the present application is based.

Advantageous Effects of Invention

The drug delivery particle of the present invention can contain a nucleic acid, a peptide, and/or a low-molecular-weight compound as a drug with viral early infection activities kept. The drug delivery particle of the present invention can also deliver the drug in a target cell-specific manner.

The method for producing a drug delivery particle according to the present invention can conveniently and efficiently introduce a drug of interest into an empty capsid or an empty particle without the need of a viral gene. As a result, a drug delivery particle that has high safety and target cell specificity can be provided.

The composition of the present invention can deliver, for example, a drug for prevention or treatment of disease, a drug for breeding, or a drug for labeling, into a cell of interest in a recipient individual.

The cell of the present invention can increase the yield of an empty capsid per unit cell.

The method for purifying an empty capsid according to the present invention can efficiently remove impurities in the method for producing a drug delivery particle.

BRIEF DESCRIPTION OF DRAWINGS

FIG. 3A shows an untreated RD line. FIG. 3B shows an RD line treated with Endo-Porter. FIG. 3C shows an RD line treated with the drug delivery particle of the present invention. FIGS. 3D and 3E show the forms of the RD cells 120 hours after the treatment with Endo-Porter and the treatment with the drug delivery particle, respectively. The scale bars in FIGS. 3A and 3B represent 50 µm, and the scale bars in FIGS. 3D and 3E represent 100 µm.

FIG. 5 is a diagram showing the affinity of a fluorescently labeled empty AAV9 capsid for muscle cells. FIG. 5A shows an untreated human fibroblast line WI-38. FIG. 5B shows a WI-38 line treated to induce muscle differentiation. The scale bars in FIGS. 5A and 5B represent 100 µm.

DESCRIPTION OF EMBODIMENTS

Figure 1:
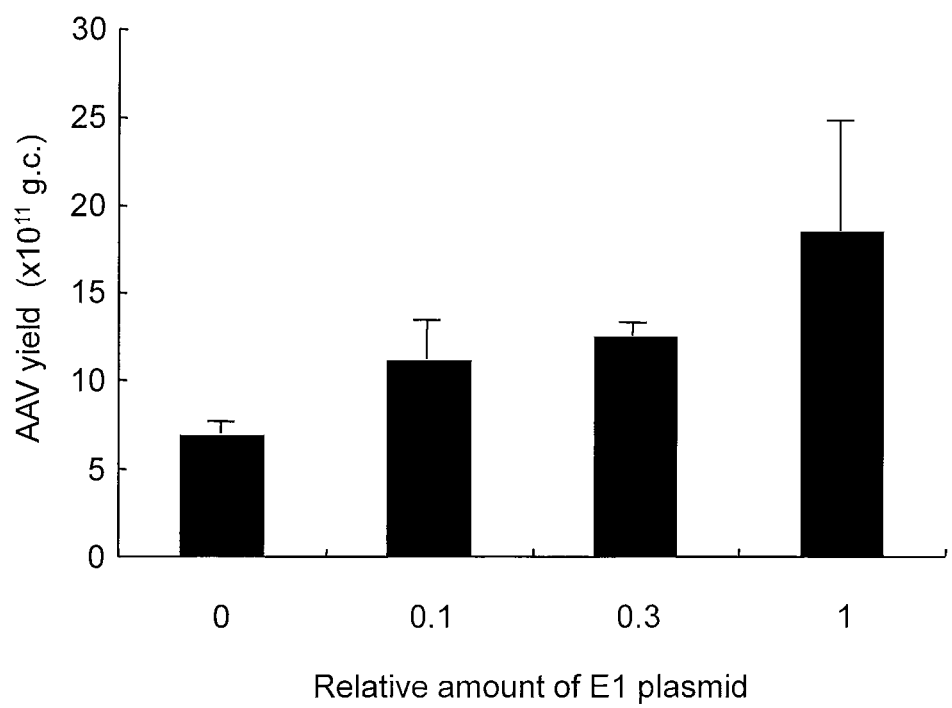
FIG. 1 is a diagram showing the relationship between the amount of an expression plasmid introduced and the amount of AAV produced, wherein E1 gene region (including an E1A gene region, an E1B19k gene, and an E2A gene region) expression plasmids were introduced in different amounts to HEK293 cells.

1. Drug Delivery Particle
1-1. Summary

The first embodiment of the present invention relates to a drug delivery particle. The drug delivery particle of the present invention comprises a drug and a capsid or an enveloped particle as components and has the ability to introduce the incorporated drug into a host cell.

1-2. Constitution

The "drug delivery particle" of the present invention comprises a capsid (1) or an enveloped particle (2) and a drug (3) contained therein as components. Hereinafter, each component will be described.

(1) Capsid

The "capsid" is a coat or a shell that is composed of a plurality of unit proteins (capsomeres) and surrounds a viral nucleic acid or a core in a virion. In the present specification, the simple term "capsid" means the structure. In the present specification, a capsid that is constituted only by a capsid protein and is free from a viral nucleic acid, a core, or other substances in the inside thereof is called an "empty capsid". In contrast to this, a capsid containing a viral nucleic acid or a core in the inside thereof is called a "nucleocapsid".

The capsid in the drug delivery particle of the present invention can be selected according to an organism species to which the drug delivery particle is applied. For example, an animal virus-derived capsid can be used in the case of using an animal as the organism species to which the drug delivery particle is applied. A plant virus-derived capsid can be used in the case of using a plant as the organism species. A bacteriophage-derived capsid can be used in the case of using a bacterium as the organism species. An animal virus-derived or plant virus-derived capsid is preferred.

When the capsid is derived from an animal virus, any animal virus included in an RNA virus group or a DNA virus group can be used. Specifically, the capsid may be derived from, for example, any RNA virus that belongs to the family Retroviridae, Picornaviridae, Caliciviridae, Astrovindae, Flaviviridae, Togaviridae, Coronaviridae, Paramyxoviridae, Rhabdoviridae, Filoviridae, Orthomyxoviridae, Bunyaviridae, Arenaviridae, Reoviridae, or Birnaviridae. Alternatively, the capsid may be derived from any DNA virus that belongs to the family Adenoviridae, Herpesviridae, Poxviridae, Iridoviridae, Hepadnaviridae, Circoviridae, Parvoviridae, or Papovaviridae. A virus belonging to the family Retroviridae in the RNA virus group or a virus belonging to the family Adenoviridae, Parvoviridae, or Herpesviridae in the DNA virus group can be preferably used as the virus from which the capsid is derived. Oncovirus, lentivirus, or spumavirus of the family Retroviridae, adenovirus of the family Adenoviridae, or AAV of the family Parvoviridae can be particularly preferably used as the virus from which the capsid is derived.

When the capsid is derived from a plant virus, any plant virus included in an RNA virus group or a DNA virus group can also be used. Specifically, the capsid may be derived from, for example, any RNA virus that belongs to the genus *Tenuivirus*, the tobamovirus group, the family Potyviridae, the dianthovirus group, the bromovirus group, the cucumovirus group, the family Rhabdoviridae, the family Reoviridae, or the cryptic virus group. Alternatively, the capsid may be derived from any DNA virus that belongs to the genus *Caulimovirus, Badnavirus*, or *Geminivirus*.

The capsomeres constituting the capsid may contain an amino acid mutation within a range capable of constituting the capsid. In this context, the "mutation" refers to the substitution, deletion, addition, or insertion of one to several amino acid(s) in an amino acid sequence constituting each capsomere. The amino acid substitution is preferably a substitution between similar amino acids. The "similar amino acids" refer to amino acids that belong to the same group classified on the basis of amino acid properties such as electric charge, side chain, polarity, and aromaticity. Examples of such groups include a basic amino acid group (arginine, lysine, and histidine), an acidic amino acid group (aspartic acid and glutamic acid), a nonpolar amino acid group (glycine, alanine, phenylalanine, valine, leucine, isoleucine, proline, methionine, and tryptophan), a polar uncharged amino acid group (serine, threonine, asparagine, glutamine, tyrosine, and cysteine), a branched amino acid group (leucine, isoleucine, and valine), an aromatic amino acid group (phenylalanine and tyrosine), a heterocyclic amino acid group (histidine, tryptophan, and proline), and an aliphatic amino acid group (glycine, alanine, leucine, isoleucine, and valine).

In the present specification, the capsid functions as a delivery carrier that contains a drug described later and deliver the drug into a target cell. Although regular icosahedral and helical capsids are broadly known, the capsid in the drug delivery particle of the present invention may be in any form that can contain a drug.

The drug delivery particle of the present invention may be constituted by a naked capsid that is not covered by an envelope described later. In such a case, this capsid itself has the original early infection activities of the virus.

In the present specification, the "infection" refers to a series of processes from the adsorption of virions onto the cell surface of host cells in which the virions then grow, to extracellular release (in the case of a naked capsid having no envelope) or budding (in the case of a capsid having an envelope, i.e., an enveloped particle described later) during the life cycle of a virus. The "early infection" refers to the stage of penetration of virions into host cells. Specifically, the early infection refers to processes from viral adsorption onto the surface of host cells, through penetration into the host cells, to uncoating caused by capsid destruction in the host cells. In contrast to this, the "late infection" refers to the stage of growth in viral infection and specifically refers to processes, for example, from the transcription of viral genes liberated into host cells or transcription after reverse transcription of viral genes and proviral integration into host chromosomes, followed by translation into viral proteins, replication of viral nucleic acids, construction of capsids by capsomeres, and packaging of the viral nucleic acids in the capsids, to the release or budding of progeny virions from the host cells.

The adsorption is achieved by proteins on capsid surface, which recognize receptors exposed on the cell surface of host cells as target molecules and adsorb the target molecules. Hence, the host cell specificity of the capsid is determined depending on the presence or absence of a receptor on the host cell. For example, human immunodeficiency virus (HIV) whose receptor is CD4 targets helper T cells having CD4 on the cell surface. Thus, the capsid of a virus capable of recognizing receptors carried by target cells and adsorbing the receptors can be used in order to confer target cell specificity to the drug delivery particle of the present invention. Referring to the example mentioned above, the drug delivery particle of the present invention can contain, as a component the capsid of HIV, which recognizes and adsorbs the receptor CD4 protein present on the cell surface of a helper T cell, in order to apply the helper T cell to the target cell of the drug delivery particle. Specifically, a feature of the drug delivery particle of the present invention is to deliver the drug of interest contained therein into the target cell by use of the original target cell-specific delivery activity of the empty capsid or the empty particle described later.

The capsid may be modified. In this context, the modification includes functional modification and labeling modification. The "functional modification" refers to a modification useful in enhancing or stabilizing the specific binding activity between the capsid and its target cell. Examples thereof include glycosylation, deglycosylation, and PEGylation. The "labeling modification" refers to a modification useful in detecting the drug delivery particle or its target cell in vivo. Examples thereof include labeling with fluorescent dyes (fluorescein, FITC, rhodamine, Texas Red, Cy3, Cy5, and Alexa Fluor (registered trademark)), fluorescent proteins (e.g., PE, APC, GFP, Venus, YFP, DsRed, and Sirius), enzymes (e.g., horseradish peroxidase, alkaline phosphatase, and glucose oxidase), radioisotopes (e.g., $^3$H, $^{14}$C, and $^{35}$S), or biotin or (strept)avidin. The modification of the capsid is not particularly limited as long as the method is capable of modifying proteins and does not influence the viral early infection activities of the capsid. Alternatively, a commercially available modification kit may be used. Examples thereof include Alexa. Fluor 568 Protein Labeling Kit (A10238) (Molecular Probes (Life Technologies Inc.)).

(2) Enveloped Particle

In the present specification, the "enveloped particle" refers to a capsid covered by an envelope. In the present specification, an empty capsid covered by an envelope as to the enveloped particle is called an "empty particle". Hereinafter, in the present specification, the capsid and the enveloped particle are collectively referred to as a "capsid, etc.", and the empty capsid and the empty particle are collectively referred to as an "empty capsid, etc.".

The "envelope" is outer covering that encloses a capsid and is carried by some viruses. The envelope is composed of a lipid bilayer studded with virus-derived glycoproteins called spikes or envelope proteins. The lipid bilayer of the envelope is a portion of a host cytoplasmic or nuclear membrane that covers the virus during budding from the host cell, and is derived from the host cell.

The enveloped particle in the drug delivery particle of the present invention is an optional component that is added according to a virus species from which the capsid used in the drug delivery particle of the present invention is derived. Specifically, when the virus from which the capsid used in the drug delivery particle of the present invention is derived is a species originally having an envelope, the enveloped particle is an essential component as a rule. This is because, in the virus species originally having an envelope, the envelope is usually responsible for adsorption and penetration functions for early infection activities to host cells. Specific examples of such virus species include influenza virus of the family Orthomyxoviridae, herpes simplex virus of the family Herpesviridae, and HIV of the family Retroviridae. On the other hand, in the case of a virus species originally having no envelope as in adenovirus or AAV or a virus species, albeit originally having an envelope, having a capsid that has all of the early infection activities in itself, the envelope can be appropriately selected, if necessary.

When the drug delivery particle of the present invention is constituted by the enveloped particle, the envelope of the enveloped particle has, of its original viral early infection activities, at least an adsorption activity and a penetration activity. On the other hand, the capsid of the enveloped particle needs only to have, of the early infection activities, at least an uncoating activity.

The viral glycoproteins serving as spikes in the envelope of the enveloped particle may have a mutation and may be modified.

(3) Drug

In the present specification, the "drug" refers to a substance to be delivered that is incorporated in the drug delivery particle of the present invention and specifically refers to a nucleic acid, a peptide, a low-molecular-weight compound, or a combination thereof. The drug can bring about biological, physical, or chemical effects on a target cell and an organism to which the drug delivery particle is applied. Examples of the biological effects include gene expression regulation such as enhancement or suppression of target gene expression, functional regulation of proteins, immune system regulation such as immunostimulation or immunosuppression, and regulation of physiological functions of cells or organisms. Examples of the physical or chemical effects include in vivo imaging (e.g., FITG, GFP, X ray, PET, MRI, or CT imaging) and tracing effects on target cells based on the labeling of the capsid, etc. or the drug. Hereinafter, each drug will be described.

(a) Nucleic Acid

In the present specification, the "nucleic acid" includes a natural nucleic acid, a chemically modified nucleic acid, an artificial nucleic acid, a nucleic acid analog, and a combination thereof.

The "natural nucleic acid" refers to a naturally occurring DNA and RNA composed of only natural nucleotides linked together. However, the natural nucleic acid of the present embodiment is an exogenous nucleic acid free from all or some genes of a virus itself from which the capsid constituting the drug delivery particle is derived. The "nucleic acid comprising all or some genes of a virus from which the capsid is derived" corresponds to, for example, the viral nucleic acid of the virus of origin or a viral vector constructed on the basis of the genes of the virus of origin.

The "chemically modified nucleic acid" refers to a nucleic acid artificially provided with chemical modification. Examples thereof include methylphosphonate-type DNA or RNA, phosphorothioate-type DNA or RNA, phosphoramidate-type DNA or RNA, and 2'-O-methyl-type DNA or RNA.

The "artificial nucleic acid" refers to a nucleic acid containing nonnatural nucleotides in a portion of a natural nucleic acid or a nucleic acid composed of only nonnatural nucleotides linked together. In this context, the "nonnatural nucleotides" refer to nucleotides artificially constructed to have properties and/or structures similar to those of the natural nucleotides, or artificially chemically modified nucleotides that do not occur naturally.

The "nucleic acid analog" refers to a high-molecular-weight compound artificially constructed to have a structure and/or properties similar to those of the natural nucleotides. Examples thereof include peptide nucleic acid (PNA), peptide nucleic acid having a phosphate group (PHONA), bridged nucleic acid/locked nucleic acid (BNA/LNA), and morpholino nucleic acid (including morpholino oligo).

The nucleic acid may have a labeled phosphate group, sugar, and/or base, if necessary. The labeling can utilize a labeling material known in the art. Examples thereof include radioisotopes (e.g., $^{32}$P, $^{3}$H, and $^{14}$C), DIG, biotin, fluorescent dyes (e.g., FITC, Texas, Cy3, Cy5, Cy7, FAM, HEX, VIC, JOE, Rox, TET, Bodipy 493, NBD, and TAMRA), and luminescent substances (e.g., acridinium ester).

Specific examples of the nucleic acid contained in the drug delivery particle include functional nucleic acids, vectors containing arbitrary genes, mRNAs or fragments thereof, and combinations thereof.

The "functional nucleic acid" refers to a nucleic acid having in vivo or intracellularly, preferably intracellularly, a particular biological function, for example, an enzymatic function, a catalytic function, or a biological inhibiting or enhancing function (e.g., inhibition or enhancement of transcription or translation). Specific examples thereof include RNA interference agents, nucleic acid aptamers (including RNA aptamers and DNA aptamers), antisense DNAs, ribozymes (including deoxyribozymes), U1 adaptors, molecular beacons, riboswitches, and transcription factor-binding sites. Particularly, an RNA interference agent can be preferably applied to the drug in the drug delivery particle. In this context, the "RNA interference agent" refers to a substance that can induce RNA interference (RNAi) in vivo so that the expression of a targeted gene can be suppressed (silenced) via the degradation of a transcript of the gene. Examples thereof include small interfering RNAs (siRNAs), short hairpin RNAs (shRNAs), and micro RNAs (miRNAs) (including pri-miRNA and pre-miRNA). The RNA interference agent undergoes in vivo degradation by nuclease in a naked RNA molecule and is thus unstable, though its gene expression suppressive effect and usefulness have already been confirmed. Hence, the effective means of delivering the RNA interference agent into a target cell has not yet been established fully. Nevertheless, the drug delivery particle of the present invention allows the drug to escape from such degradation by nuclease or the like until delivery into a target cell even after in vivo administration, because the drug is protected within the capsid. The drug delivery particle can comprise two or more functional nucleic acids in the empty capsid, etc.

The "vector" includes, for example, a viral vector, a plasmid, a cosmid, and an artificial chromosome. The artificial chromosome includes a human artificial chromosome (HAC), a yeast artificial chromosome (YAC), a bacterial artificial chromosome (BAC), and a P1-derived artificial chromosome (PAC). HAC is preferred. As mentioned above, the viral vector excludes a viral vector constructed on the basis of the genes of a virus from which the capsid is derived.

Each vector can contain an arbitrary gene other than the genes of a virus from which the capsid constituting the drug delivery particle is derived, or a fragment thereof. Examples thereof include transcription factors, signaling factors, genes encoding extracellularly secretory proteins or enzymes, and fragments having their activities. The gene contained in the vector may be any wild-type gene or mutant gene. Alternatively, two or more vectors containing different genes may be contained as the drug.

In the drug delivery particle of the present invention, each vector is preferably contained in a state capable of expressing the gene or the fragment thereof in a target cell. In this context, the phrase "state capable of expressing" means a state where the gene or the fragment thereof contained in the vector is placed so as to be expressible in a target cell under the control of a promoter and a terminator in a nucleic acid expression system. The "nucleic acid expression system" refers to a system having at least one set of expression regulatory elements necessary for gene expression, in a state of capable of functioning. The expression regulatory elements include the promoter and the terminator as well as, if necessary, an enhancer and a poly A addition signal.

The promoter must be operable in a target cell containing the introduced nucleic acid. Hence, a promoter derived from an organism species to which the drug delivery particle is applied, or a related species thereof is preferred. In the case of, for example, a drug delivery particle intended for administration to a human, the promoter is preferably human-derived. Although promoters such as overexpression-type promoters, constitutive promoters, site-specific promoters, stage-specific promoters, and inducible promoters are known according to expression patterns, any promoter can be used in the drug delivery particle. The promoter can be appropriately selected according to the desired expression pattern in a recipient cell.

The terminator is not particularly limited as long as its sequence can terminate the transcription of the gene transcribed by the action of the promoter. The terminator is preferably a terminator derived from the same organism species as in the promoter, more preferably a terminator that pairs with the promoter on the genome of the organism species from which the promoter is derived.

The enhancer is not particularly limited as long as its sequence can enhance the expression efficiency of the gene or the fragment thereof in the vector. The enhancer derived from the same organism species as in the promoter is preferred.

Specific examples of the nucleic acid expression system thus constituted include expression vectors.

Each vector can also contain a selective or labeling marker gene for confirming the successful delivery of the nucleic acid as the drug into the target cell. Examples of the labeling or selective marker gene include drug resistance genes, fluorescent or luminescent reporter genes (e.g., luciferase, β-galactosidase, β-glucuronidase (GUS), and GFP genes), and enzyme genes.

The drug delivery particle of the present invention may further contain an "mRNA" encoding an arbitrary protein, or a fragment thereof. The mRNA may be any of mRNA precursors and mature mRNAs. A mature mRNA is preferred. The mRNA or the fragment thereof may also contain a 5'-terminal m7G cap structure and/or a 3'-terminal poly A strand. The protein encoded by the mRNA may be any wild type or mutant.

The size of the nucleic acid is not limited as long as the size allows the nucleic acid to be contained in the capsid. Since the internal capacity of the capsid differs depending on the type of the virus of origin, the base number of the nucleic acid contained therein also depends on the virus species from which the capsid is derived. The size of the nucleic acid is usually 50 kb or smaller, preferably 20 kb or smaller, more preferably 10 kb or smaller, further preferably 5 kb or smaller.

(b) Peptide

In the present specification, the peptide includes both of an oligopeptide and a polypeptide. Specific examples of the oligopeptide include peptide hormones and polypeptide fragments. Specific examples of the polypeptide include antibodies, transcription factors, signaling factors, and enzymes.

The antibody includes, for example, a monoclonal antibody, a polyclonal antibody, a recombinant antibody, a synthetic antibody, and an antibody fragment.

When the antibody is a polyclonal antibody or a monoclonal antibody, its immunoglobulin molecule may be of any class (e.g., IgG, IgE, IgM, IgA, IgD, and IgY) or of any subclass (e.g., IgG1, IgG2, IgG3, IgG4, IgA1, and IgA2). In the case of using a monoclonal antibody or a polyclonal antibody as the drug, the antibody is preferably an antibody derived from the same species as a recipient organism species of the drug delivery particle. The drug delivery particle may be administered to, for example, a human. In such a case, the monoclonal antibody or the polyclonal antibody used as the drug is preferably a human antibody.

The "recombinant antibody" refers to a chimeric antibody, a humanized antibody, or a polyspecific antibody. The "chimeric antibody" refers to an antibody that is prepared using the amino acid sequences of antibodies derived from different animals in combination. This antibody is composed of a certain antibody with constant regions (C regions) replaced with the C regions of another antibody. The chimeric antibody corresponds to, for example, an antibody composed of a mouse monoclonal antibody with C regions replaced with the C regions of a human antibody. As a result, the immune response of a human body to the antibody can be alleviated. The "humanized antibody" refers to a mosaic antibody composed of an antibody of a nonhuman mammal, for example, a mouse antibody, with V region complementarity-determining regions (CDRs) replaced with the CDRs of a human antibody. The "polyspecific antibody" refers to a polyvalent antibody, i.e., an antibody having a plurality of antigen-binding sites in one molecule, wherein these antigen-binding sites bind to different epitopes, respectively. Examples thereof include bispecific antibodies that have two antigen-binding sites as in IgG, wherein these antigen-binding sites bind to different epitopes, respectively.

The "synthetic antibody" refers to an antibody synthesized chemically or using a recombinant DNA method. Examples thereof include antibodies newly synthesized using a recombinant DNA method. Specific examples thereof include single chain fragment of variable region (scFv), diabody, triabody, and tetrabody.

The "antibody fragment" corresponds to, for example, Fab, F(ab'$_2$), or Fv.

The peptide may be modified. The modification of the peptide includes functional modification and labeling modification. Examples of the functional modification include glycosylation, acetylation, formylation, amidation, phosphorylation, and PEGylation. Examples of the labeling modification include labeling with fluorescent dyes (fluorescein, FITC, rhodamine, Texas Red, Cy3, and Cy5), fluorescent proteins (e.g., PE, APC, and GFP), enzymes (e.g., horseradish peroxidase, alkaline phosphatase, and glucose oxidase), radioisotopes (e.g., $^3$H, $^{14}$C, and $^{35}$S), or biotin or (strept)avidin.

The size of the peptide is not limited as long as the size allows the peptide to be contained in the capsid. In general, the internal capacity of the capsid differs depending on the type of the virus of origin, and even peptides composed of the same number of amino acids differ in the success or failure of introduction into the capsid, depending on their three-dimensional structures. The size of the peptide can therefore be appropriately determined in consideration of these factors. The size is usually 500 kDa or smaller, preferably 100 kDa or smaller, more preferably 80 kDa or smaller, further preferably 50 kDa or smaller.

(c) Low-Molecular-Weight Compound

In the present specification, the "low-molecular-weight compound" refers to a compound having a molecular weight of 5000 or lower, preferably 2000 or lower, more preferably 1000 or lower and corresponds to a substance other than the nucleic acid or the peptide. Examples thereof include various pharmaceutical compounds such as hormones (e.g., steroid hormones such as androgen, estrogen, progesterone, aldosterone, and cortisol), neurotransmitters (e.g., adrenaline, epinephrine, noradrenaline, and dopamine), histone deacetylase inhibitors, and immunosuppressive agents. Also, the low-molecular-weight compound includes a derivative of a particular low-molecular-weight compound having a pharmacological activity equivalent to that of the low-molecular-weight compound, or a salt thereof.

1-3. Effect

The drug delivery particle of the present invention, unlike a viral vector, is free from virus-derived genes and as such, has high safety even after application and can contain, as a drug, a peptide or a low-molecular-weight compound which has conventionally been difficult to introduce into a capsid. The drug delivery particle of the present invention can also deliver the drug into a particular cell by virtue of a target cell-specific delivery activity based on the serotype of the capsid or the envelope constituting the drug delivery particle.

The drug delivery particle of the present invention has the early infection activities of the component capsid, etc. involved in the stage of viral penetration into a host cell, but lacks late infectivity involved in the stage of viral growth because the drug delivery particle is free from a nucleic acid comprising all or some genes of a virus from which the capsid, etc. is derived. Thus, the application of the drug delivery particle of the present invention allows the incorporated drug to be delivered into a target cell via endocytosis or membrane fusion, but neither disrupts the physiological functions of the target cell in relation to virion growth in the target cell nor injures the cell membrane of a host cell in relation to the release or budding of the virion from the host cell. The functional analysis of various molecules or genes can therefore be achieved without influencing cell functions.

2. Method for Producing Drug Delivery Particle

2-1. Summary

The second embodiment of the present invention relates to a method for producing a drug delivery particle.

In spite of the previous proposals, as mentioned above, to express empty AAV capsids and use the resulting capsids as drug delivery carriers, the technique of introducing drugs as substances to be delivered into empty capsids with viral early infection activities kept has not yet been established. The production method of the present invention can produce the drug delivery particle of the first embodiment by a convenient method for introducing a drug to the inside of an empty capsid, etc. with its viral early infection activities kept.

2-2. Production Method

The production method of the present invention comprises a mixing step (1) and an introduction step (2). The production method of the present invention can further comprise a removal step (3), if necessary. Hereinafter, each step will be described specifically. In the production method of the present invention, desirably, a series of steps is performed under aseptic conditions in order to prevent contamination or the like.

(1) Mixing Step

The "mixing step" refers to a step of mixing an empty capsid, etc. with a drug in a solution comprising a surfactant.

Any capsid, etc. derived from each virus described in the first embodiment can be used as the empty capsid, etc. The preparation of the empty capsid, etc. will be described later. The empty capsid, etc. is preferably used in this step after purification treatment. This is because coexistence with impurities including proteins of host cells reduces drug introduction efficiency in the subsequent introduction step.

Any drug described in the first embodiment can be used as the drug. Two or more different drugs may be introduced into one empty capsid, etc. In this case, these two or more different drugs can be added into the solution. Unlike the first embodiment, the present embodiment can employ all or some genes of a virus itself from which the empty capsid, etc. used is derived, if necessary, as the drug. For example, the viral nucleic acid of the virus of origin or a viral vector constructed on the basis of the genes of the virus of origin may be used as the drug.

The surfactant used in this step is not particularly limited, and any of nonionic surfactants such as Triton X-100, Triton X-114, NP-40, Brij-35, Brij-58, Tween-20, Tween-80, octyl-β-glucoside, and OTG, nonionic polymer surfactants such as a copolymer of PEG and PPG, anionic surfactants such as SDS, amphoteric surfactants such as CHAPS and CHAPSO, and combinations thereof can be used. A nonionic surfactant is preferred.

The "solution comprising a surfactant" refers to a solution containing the surfactant dissolved in an appropriate solvent. Examples of the solvent include water (including distilled water, sterile water, and deionized water), physiological saline, and phosphate buffers. Water is preferred. The concentration of the surfactant in the solution is 0.1% to 20%, preferably 1% to 20%, more preferably 3% to 18%, further preferably 5% to 15%, in terms of % by volume.

The volume ratio or mass ratio between the empty capsid, etc. and the drug mixed into the solution comprising a surfactant can be appropriately determined according to the type of the drug to be introduced into the empty capsid, etc.

After the addition of the empty capsid, etc. and the drug into the solution comprising a surfactant, the amount of the resulting solution can be adjusted, if necessary, with a buffer such as PBS and fully mixed by stirring using a stirrer, a stirring bar, or the like to prepare a mixed solution.

(2) Introduction Step

The "introduction step" refers to a step of keeping the mixed solution obtained in the mixing step, at a predetermined temperature to introduce the drug into the empty capsid, etc.

The keeping temperature can be in the range of −5 to 50° C. This is because the mixed solution is likely to freeze at a temperature lower than −5° C., whereas the empty capsid, etc. and/or the drug is likely to be denatured and/or inactivated at a temperature higher than 50° C. A temperature of 0 to 40° C. or 4 to 35° C. is preferred.

The time for which the mixed solution is kept is not limited and is preferably 5 minutes to 120 minutes after the mixing. This is because a time shorter than 5 minutes is insufficient for the introduction of the drug, whereas keeping for a time longer than 120 minutes is not expected to increase introduction efficiency. A time of 10 minutes to 90 minutes or 15 minutes to 60 minutes is more preferred.

In this step, the mixed solution needs only to be left standing at the keeping temperature for the keeping time. The mixed solution may be mildly stirred, if necessary.

In this step, the drug is introduced into the empty capsid, etc. treated with the surfactant to obtain the drug delivery particle of the present invention.

(3) Removal Step

The "removal step" refers to a step of removing the surfactant in the solution after the introduction step. This step is an optional step and can be performed, if necessary.

The method for producing a drug delivery particle according to the present invention employs a surfactant for the introduction of the drug into the empty capsid, etc. Although the drug delivery particle may be produced by the introduction step, the solution containing the drug delivery particle after the introduction step coexists with the surfactant used. When such a drug delivery particle is applied to an organism, this surfactant may usually adversely affect the organism. Hence, the surfactant is preferably removed by this step for using the produced drug delivery particle as an active ingredient in a composition described later.

The surfactant can be removed by any method known in the art that is capable of removing the surfactant from the solution, without particular limitations. Examples thereof include removal methods using ultrafiltration membranes and removal methods using dialysis operation through dialysis membranes or dialysis cassettes. The capsid or the enveloped particle in the drug delivery particle usually has a size of 10 nm or larger. Thus, the mixed solution after the introduction step can be circulated using an ultrafiltration membrane having a pore size smaller than 10 nm, i.e., a molecular weight cutoff of 100 kMW or lower, to thereby separate and remove the surfactant in the solution after the introduction step while recovering the drug delivery particle. Also, a free drug that has not been incorporated into the empty capsid, etc. may adversely affect, depending on its type, an organism to which the drug delivery particle is applied. This method, however, can conveniently separate and remove such a free drug in the solution after the introduction step, simultaneously with the surfactant. In this context, the method using an ultrafiltration membrane cannot remove an empty capsid, etc. that has not incorporated the drug therein in the introduction step. Since the empty capsid, etc., however, has early infection activities but lacks a late infection activity, as mentioned above, the empty capsid, etc. can coexist with the drug delivery particle without problems.

2-3. Method for Preparing Empty Capsid, Etc.

The empty capsid, etc. used in the mixing step of the present embodiment can be prepared directly from a virus-infected host cell. Alternatively, a recombinant capsid may be prepared for the purpose of obtaining the empty capsid alone.

(Method for Preparation from Virus-Infected Host Cell)

The empty capsid, etc. is usually formed while a virus grows in a virus-infected host cell to construct a progeny virion. Thus, the empty capsid, etc. can be prepared directly from an extract of the virus-infected host cell or from a culture solution after release or budding of the virion. In this case, the empty capsid, etc. coexists with the virion in the host cell extract or culture solution. Hence, the virion is preferably separated from the host cell extract or culture solution or inactivated to purify the empty capsid, etc. These procedures can be performed using a method known in the art. Examples of the methods for separating the virion and preparing the empty capsid, etc. include density-gradient centrifugation methods using cesium chloride and a method using an ion-exchange membrane described in JP Patent Publication (Kokai) No. 2007-117003 A (2007).

Meanwhile, viruses such as AAV cannot autonomously grow. Their growth requires the coinfection of host cells by helper viruses as a rule. Thus, such viruses do not grow in helper virus-uninfected cells even if the cells are infected thereby. These viruses can be used without the need for inactivating or removing virions after host cell extraction. Accordingly, such a virus is preferred as a virus from which the empty capsid used in the method for producing a drug delivery particle according to the present invention is derived. Particularly, AAV itself is free from known pathogenicity and is therefore more preferred because of its high safety. The production, in a host cell, of an empty capsid, etc. derived from a virus that requires a helper virus requires coinfecting the host cell by the virus and the helper virus or expressing some genes of the helper virus (helper genes) either preliminarily or simultaneously with the viral genes in the host cell.

Hereinafter, a method for preparing an AAV-derived empty capsid from a host cell will be described as an example.

The growth of AAV in a host cell requires, of course, the genes of AAV itself, i.e., a Rep gene involved in AAV replication and a Cap gene encoding a capsid protein, and inverted terminal repeats (ITRs) located at the 5' and 3' ends of a sequence comprising these genes. Expression vectors or the like containing these genes are introduced into arbitrary host cells that can be infected by AAV, for example, by a transformation or transfection method known in the art, to infect the host cells by AAV. Empty capsids can be recovered from the host cells thus infected or from a culture solution thereof. The empty capsids can be recovered from the host cells using a method known in the art. For example, the host cells are homogenized, and the empty capsids can be recovered from the resulting cell extract by a method described later in Examples.

Alternatively, host cells endogenously having some adenovirus genes may be used in AAV replication and growth. Examples thereof include use of human embryonic kidney cell line HEK293 cells (in the present specification, also abbreviated to "293 cells") endogenously having an adenovirus E1A gene region and E1B19k gene (in the present specification, they are also collectively referred to as an "E1 gene region"). In the case of AAV replication and growth using 293 cells, only an adenovirus E2A gene region, E4orf6 gene, and VA RNA-encoding gene can be introduced as helper genes into the 293 cells. This approach does not require introducing the E1 gene region and as such, is suitable for the production of AAV-derived empty capsids.

In order to improve the production efficiency of AAV-derived empty capsids per host cell, an adenovirus E1 gene region may be further introduced, together with the helper genes, into the 293 cells to prepare a cell line having the enhanced ability to produce AAV. As described above, the 293 cells already contain the adenovirus E1 gene region and therefore usually do not require introducing the E1 gene region. Nevertheless, the present inventors have found that, as shown in Example 1 described later, 293 cells containing E1 gene region expression plasmids introduced simultaneously with other plasmids containing helper genes, etc., exhibit a higher titer of AAV and enhanced AAV production, compared with 293 cells in which only helper genes are introduced. Details about this mechanism are uncertain. E1 gene products function as master switches for the expression of adenovirus early genes (Matsushita, T., et al., 2004, J. Gen. Virol., 85: 2209-2214). Presumably, the higher intracellular expression level of the E1 gene region than that in normal 293 cells was able to further enhance the expression levels of downstream genes of the adenovirus, resulting in the production of AAV-derived empty capsids in larger amounts from host cells.

The preparation of the cell line having the enhanced ability to produce AAV can be achieved by introducing, for example, expression vectors containing expressible inserts of an E1 gene region, an E2A gene region, an E4orf6 gene, and a VA RNA-encoding gene, respectively, into 293 cells. After the introduction of the expression vectors containing each of these genes or gene regions into 293 cells, 293 cells capable of stably expressing one or more set(s) consisting of the E1 gene region, the E2A gene region, the E4orf6 gene, and the VA RNA-encoding gene are selected, if necessary, and the lineage of these newly prepared cells can also be used.

In the case of AAV production using the cell line having the enhanced ability to produce AAV, the necessary AAV genes (Rep gene, Cap gene, ITRs, etc.) can be introduced in a state capable of being expressed or functioning into the cell line.

Further, expression vectors containing a Bcl-$x_L$ gene derived from the organism species of the host cell may be introduced together with the expression vectors containing the E1 gene region. From the previous research, Bcl-$x_L$ is known to complement the functions of the E1B19k gene (Matsushita et al., J. Gen. Virol., 2004, 85: 2209-2214). As shown in Example 2 described later, the E1 gene region can be further activated. Also, Bcl-$x_L$ has the effect of suppressing cell death (apoptosis) (Yamaguchi et al., Gene Ther., 2003, 10: 375-85). Thus, cytotoxicity associated with gene transfer operation can also be suppressed.

Alternatively, an established cell line may be used which is capable of stably expressing an E1 gene region expression vector and/or a Bcl-$x_L$ gene expression vector introduced in 293 cells. Examples thereof include a HEK293EB line described later in Example 2.

(Method for Preparing Recombinant Empty Capsid, Etc.)

In the case of preparing the empty capsid, etc. alone, expression vectors containing the desired viral Cap gene may be expressed in appropriate host cells. For example, if the recombinant empty capsid, etc. of AAV is necessary, it is only required to insert a nucleotide sequence comprising the Cap gene of the desired AAV serotype (specifically, for example, an AAV1 Cap gene consisting of the nucleotide sequence represented by SEQ ID NO: 1, an AAV2 Cap gene consisting of the nucleotide sequence represented by SEQ ID NO: 2, an AAV5 Cap gene consisting of the nucleotide sequence represented by SEQ ID NO: 3, an AAV6 Cap gene consisting of the nucleotide sequence represented by SEQ ID NO: 4, an AAV7 Cap gene consisting of the nucleotide sequence represented by SEQ ID NO: 5, an AAV8 Cap gene consisting of the nucleotide sequence represented by SEQ ID NO: 6, or an AAV9 Cap gene consisting of the nucleotide sequence represented by SEQ ID NO: 7) into an appropriate expression vector. After expression of the Cap gene in host cells, the recombinant empty capsid, etc. can be obtained from a cell extract of the host cells homogenized or from a culture solution of the host cells. The recombinant empty capsid, etc. can be recovered from the cell extract or the culture solution by a method known in the art.

This method does not require adenovirus-derived helper genes and can employ any type of expression vector that permits expression in host cells. For example, expression vectors for bacteria, *Bacillus subtilis*, yeasts, insect cells, animal cells, or plant cells can be used. In this context, for example, pET21α series, pGEX4T series, pUC118 series, pUC119 series, pUC18 series, or pUC19 series can be used as expression vectors for *E. coli*. For example, pUB110 series or pTP5 series can be used as expression vectors derived from *Bacillus subtilis*. For example, YEp13 series, YEp24 series, or YCp50 series can be used as yeast-derived expression vectors. Baculovirus can be used as an expression vector for insect cells. pUC18 series or pUC19 series (e.g., pA1-11, pXT1, pRc/CMV, pRc/RSV, and pcDNAI/Neo) can be used as expression vectors for animal cells. For example, pRI series or pGW series binary vectors can be used as expression vectors for plant cells. Such expression vectors are also available from each manufacturer (Novagen (Merck KGaA), Takara Shuzo Co., Ltd., Daiichi Pure Chemicals Co., Ltd., Qiagen N.V., Stratagene Corp., Promega Corp., Roche Diagnostics K.K., Invitrogen Corp., Genetics Institute, Inc., GE Healthcare Japan Corp., etc.).

Each Cap gene can be inserted into these expression vectors using a recombinant gene technique known in the art. See a method described in, for example, Sambrook, J. et al., (1989) Molecular Cloning: A Laboratory Manual Second Ed., Cold Spring Harbor Laboratory Press, Cold Spring Harbor, N.Y.

2-4. Method for Purifying Empty Capsid

The AAV-derived empty capsid can be purified from the cell homogenate on the basis of a purification method known in the art. The AAV-derived empty capsid can be purified by, for example, a cesium density-gradient ultracentrifugation method, which is a general method. Alternatively, purification methods using various chromatography techniques including ion-exchange chromatography are disclosed in, for example, JP Patent No. 3313117, JP Patent Publication (Kohyo) No. 2000-510682 A (2000), JP Patent Publication (Kohyo) No. 11-511326 A (1999), JP Patent Publication (Kohyo) No. 2001-513644 A (2001), JP Patent Publication (Kohyo) No. 2001-514845 A (2001), or U.S. Pat. No. 6,593,123. These methods may be used in the purification. In addition, a purification method which involves separating empty capsids from virions using an ion-exchange membrane, which is disclosed in JP Patent Publication (Kokai) No. 2007-117003 A (2007), may be used.

Unfortunately, the purification method based on the cesium density-gradient ultracentrifugation method may insufficiently separate the empty capsid, etc. from virions due to their similar specific gravities. The purification methods using various chromatography techniques employ columns packed with beads and therefore result in insufficient diffusion of samples. In addition, these methods also present problems associated with purification efficiency such as time-consuming adsorption and elution, due to low efficiency of sample adsorption onto the columns and the large capacity of the columns. The method using an ion-exchange membrane often presents the problem of contamination by impurities such as soluble proteins even after purification.

The present inventor has developed a novel purification method for conveniently removing soluble proteins, comprising heating a host cell extract or culture solution at a predetermined temperature to coagulate coexisting soluble proteins. This purification method can be used in the purification of not only the empty capsid, etc. but virions containing viral genomes as in viral vectors. In general, a method which involves coagulating soluble proteins by heating and then removing the resulting proteins is well known. By contrast, a method which involves purifying the empty capsid, etc. or virions under temperature and heating time conditions shown below to remove soluble proteins has been unknown so far. The predetermined heating temperature for purifying the empty capsid, etc. or virions is preferably in the range of 45 to 60° C. This is because soluble proteins may not be coagulated at a temperature lower than 45° C. due to insufficient denaturation, whereas the empty capsid, etc. of interest or the virions may be denatured at a temperature higher than 60° C. and thereby lose its viral early infection activities. The temperature is more preferably in the range of 48 to 58° C., further preferably in the range of 50 to 55° C.

The heating time varies depending on the heating temperature. The heating time is preferably 3 minutes to 30 minutes, more preferably 5 minutes to 20 minutes, further preferably 5 minutes to 10 minutes, in the case of a heating temperature of, for example, 55 to 60° C. This is because heating for a time longer than 30 minutes in the range of 55 to 60° C. may thermally denature the empty capsid, etc., which in turn loses its early infection activities. On the other hand, the heating time is preferably 10 minutes to 90 minutes, more preferably 15 minutes to 60 minutes, further preferably 20 minutes to 40 minutes, in the case of a heating temperature of 45° C. or higher and lower than 55° C. This is because heating for a time shorter than 10 minutes in the temperature range of 45° C. or higher and lower than 55° C. may not coagulate soluble proteins due to insufficient denaturation. Thus, the heating time can be appropriately determined within the range described above in consideration of the heating temperature.

The method for the heating treatment is not particularly limited. The host cell extract or culture solution can be heated over direct heat, on a hot plate, by microwave (microwave oven) or induction heating (IH), in hot water, etc. The soluble proteins coagulated or aggregated by the heat treatment may be removed by a method known in the art. Examples thereof include a method which involves precipitating the coagulated proteins by centrifugation and recovering the supernatant, and a method which involves filtering off the coagulated proteins. The method for purifying an empty capsid, etc. or a virion by heat treatment according to the present invention may be combined with one or more of the purification methods known in the art. For example, the method for purifying an empty capsid, etc. or a virion by heat treatment according to the present invention is effective for removing soluble proteins as impurities, but cannot separate the empty capsid, etc. from virions. The purification method of the present invention, however, can be combined with, for example, the method using an ion-exchange membrane described in JP Patent Publication (Kokai) No. 2007-117003 A (2007) to thereby purify only the empty capsid at a high purity.

2-5. Effect

The production method of the present invention can produce a drug delivery particle by conveniently and efficiently introducing a drug into an empty capsid, etc. without deleting the early infection activities of the empty capsid, etc. The drug delivery particle obtained by the production method of the present invention is highly safety without a viral growth activity because the empty capsid, etc. used lacks a viral late infection activity.

The method for preparing an empty AAV particle according to the present invention can enhance the amount of AAV produced per host cell and can therefore prepare a larger number of empty particles.

The method for purifying an empty particle, etc. or a virion according to the present invention can conveniently remove soluble proteins in a host cell extract or a host cell culture solution, which have conventionally been difficult to sufficiently remove.

3. Drug Composition 3-1. Summary

The third embodiment of the present invention relates to a drug composition. A feature of the drug composition of the present invention is to comprise at least one drug delivery particle of the first embodiment and/or at least one drug delivery particle obtained by the production method of the second embodiment as an active ingredient.

3-2. Constitution

In the present specification, the "drug composition" refers to a composition intended for conferring some physiological effect to an organism to which the drug composition is applied, or its cells by the action of a drug contained in the drug delivery particle serving as an active ingredient. Examples of such physiological effects include disease or disease damage resistance, drug resistance or sensitivity, enhancement or suppression of physiological activities, and/or novel characters. In the present specification, a drug composition that is applied to an animal, particularly, a human, as the organism and intended for the prevention, diagnosis, and/or treatment of disease by the action of the active ingredient is particularly referred to as a "pharmaceutical composition". In the present specification, the "prevention" refers to the act of stopping disease or disease damage from being developed. The "treatment" refers to the act of alleviating or removing the developed disease or disease damage and/or symptoms associated therewith.

The drug composition of the present invention comprises the drug delivery particle as an active ingredient and can further comprise a carrier and/or an additional drug having the same or different pharmacological effect as or from that of the drug contained in the drug delivery particle.

(Drug Delivery Particle)

The drug delivery particle of the present embodiment is the drug delivery particle of the first embodiment or the drug delivery particle obtained by the production method of the second embodiment. One drug composition may comprise two or more different drug delivery particles. In this case, the drug delivery particles may have capsids, etc. derived from viruses different from each other and/or drugs of types different from each other. The drug composition may comprise, for example, drug delivery particles differing in target cells.

The content of the drug delivery particle in the drug composition differs depending on the type and/or effective amount of the drug contained in the drug delivery particle, recipient cells, the type of disease or disease damage, the formulation (including form and size) of the drug composition, and the type of a carrier described later and is appropriately determined in consideration of these conditions.

In the present specification, the "effective amount" refers to an amount that is required for the drug contained in the drug delivery particle to exert functions as an active ingredient and confers few or no undesired harmful adverse reactions to an organism to which the drug composition is applied. This effective amount can vary depending on various conditions such as information about a subject and an administration route.

In this context, the "subject" refers to an organism (including an animal and a plant) to which the drug composition is applied. A subject which is a human is particularly referred to as a "human subject". Also, the "information about a subject" refers to various pieces of individual information about the organism to which the drug composition is applied and includes, for example, general health conditions, the degree of progression or severity of disease or disease damage, if developed, age, body weight, sex, diet, drug sensitivity, the presence or absence of concurrent medication, and resistance to treatment in the case of a human subject. The final effective amount of the drug delivery particle and the amount of the drug composition applied calculated on the basis thereof can be determined finally by the judgment of a physician, a dentist, a veterinarian, or a plant doctor or the like according to, for example, information about an individual subject.

(Carrier)

The "carrier" refers to a substance that is added without inhibiting or suppressing drug action, in order to facilitate the formulation of the drug composition or its application to an organism and maintain the effect of the drug contained in the drug delivery particle.

When the drug composition is applied to an animal, examples of the carrier include excipients, binders, disintegrants, fillers, emulsifiers, flow control additives, and lubricants.

Examples of the "excipient" include sugars such as monosaccharides, disaccharides, cyclodextrin, and polysaccharides (specifically including, but not limited to, glucose, sucrose, lactose, raffinose, mannitol, sorbitol, inositol, dextrin, maltodextrin, starch, and cellulose), metal salts (e.g., sodium phosphate, calcium phosphate, calcium sulfate, and magnesium sulfate), citric acid, tartaric acid, glycine, low-, medium-, or high-molecular-weight polyethylene glycol (PEG), Pluronic, and combinations thereof.

Examples of the "binder" include starch paste made of corn, wheat, rice, or potato starch, gelatin, tragacanth, methylcellulose, hydroxypropylmethylcellulose, carboxymethylcellulose sodium, polyvinylpyrrolidone.

Examples of the "disintegrant" include the starch described above, carboxymethyl starch, cross-linked polyvinylpyrrolidone, agar, alginic acid, sodium alginate, and salts thereof.

Examples of the "filler" include the sugar described above, calcium phosphate (e.g., tricalcium phosphate and calcium hydrogen phosphate).

Examples of the "emulsifier" include sorbitan fatty acid ester, glycerin fatty acid ester, sucrose fatty acid ester, and propylene glycol fatty acid ester.

Examples of the "flow control additive" and the "lubricant" include silicate, talc, stearate, and polyethylene glycol.

Such a carrier may be appropriately used according to the need. The drug composition of the present invention can also comprise, in addition to these additives, a corrigent, a dissolution aid (solubilizer), a suspending agent, a diluent, a surfactant, a stabilizer, an absorption promoter (e.g., quaternary ammonium salts and sodium lauryl sulfate), an expander, a wetting agent, a humectant (e.g., glycerin and starch), an adsorbent (e.g., starch, lactose, kaolin, bentonite, and colloidal silicic acid), a disintegration inhibitor (e.g., white sugar, stearin, cacao butter, and hydrogenated oil), a coating agent, a colorant, a preservative, an antioxidant, a perfume, a flavor, a sweetener, a buffer, etc., if necessary.

When the drug composition is applied to a plant, examples of the carrier include natural mineral powders, synthetic mineral powders, emulsifiers, dispersants, and surfactants.

The "natural mineral powder" corresponds to, for example, kaolin, clay, talc, and chalk.

The "synthetic mineral powder" corresponds to, for example, highly dispersible silica and silicate.

The "emulsifier" corresponds to nonionic and anionic emulsifiers (e.g., polyoxyethylene fatty alcohol ether, alkyl sulfonate, and aryl sulfonate).

Examples of the "dispersant" include lignosulfite waste liquors and methylcellulose.

The "surfactant" corresponds to, for example, alkali metal salts, alkaline earth metal salts, and ammonium salts of lignosulfonic acid, naphthalenesulfonic acid, phenolsulfonic acid, or dibutylnaphthalenesulfonic acid, alkylaryl sulfonate, alkyl sulfate, alkyl sulfonate, fatty alcohol sulfate, fatty acid and sulfated fatty alcohol glycol ether, condensates of sulfonated naphthalene or naphthalene derivatives and formaldehyde, condensates of naphthalene or naphthalenesulfonic acid, phenol, and formaldehyde, polyoxyethylene octylphenyl ether, ethoxylated isooctylphenol, octylphenol, nonylphenol, alkylphenyl polyglycol ether, tributylphenyl polyglycol ether, tristearylphenyl polyglycol ether, alkylaryl polyether alcohol, alcohol and fatty alcohol/ethylene oxide condensates, ethoxylated castor oil, polyoxyethylene alkyl ether, ethoxylated polyoxypropylene, lauryl alcohol polyglycol ether acetal, sorbitol ester, lignosulfite waste liquors, and methylcellulose.

One drug composition of the present embodiment can contain one or more of these carriers.

In this context, a pharmaceutically acceptable carrier is used in the pharmaceutical composition, while an agriculturally acceptable carrier is used for plants.

(Additional Drug)

The drug composition of the present invention can contain one or more additional drug(s) having the same or different pharmacological effect as or from that of the drug contained in the drug delivery particle without inhibiting or suppressing the action of the drug delivery particle serving as an active ingredient. In the case of, for example, a human subject, there may exist another disease that is likely to occur in conjunction with the disease to be treated. In such a case, the drug composition (pharmaceutical composition) may comprise a therapeutic agent for another disease. In the case of a plant subject, the drug composition may comprise, for example, an insecticide, a germicide, and/or a fertilizer.

3-3. Formulation

The formulation of the drug composition differs depending on an application method and/or prescription conditions. Administration methods for drug administration to animals can usually be broadly classified into oral and parenteral administration methods. This will be described later.

Examples of formulations suitable for oral administration can include solid preparations (including tablets, pills, sublingual preparations, capsules, drops, and troches), granules, dusts, powders, and liquid preparations. The solid preparations can be prepared, if necessary, as coated formulations known in the art, for example, sugar-coated tablets, gelatin-coated tablets, enteric coated tablets, film-coated tablets, bilayer tablets, or multilayer tablets.

The parenteral administration is subdivided into systemic administration and local administration. The local administration is further subdivided into interstitial administration, transepidermal administration, transmucosal administration, and transrectal administration. The drug composition can also be prepared as a formulation suitable for each administration method. Examples of formulations suitable for systemic or interstitial administration include injections which are liquid preparations. Examples of formulations suitable for transepidermal administration or transmucosal administration can include liquid preparations (including liniments, eye drops, nasal drops, and inhalants), suspensions (including emulsions and creams), powders (including nasal drops and inhalants), pastes, gels, ointments, and plasters. Examples of formulations suitable for transrectal administration can include suppositories.

In the case of drug administration to plants, examples of the formulation of the drug composition include liquids, solids (including semi-solids), and combinations thereof. In this case, the drug composition can be prepared as solutions, oil dispersions, emulsions, suspensions, dusts, powders, pastes, gels, pellets, tablets, and granules.

In this context, the respective specific shapes or sizes of these formulations can fall within ranges accepted for each formulation known in the art, without particular limitations.

3-4. Production of Drug Composition

The drug composition of the present invention can be formulated using a method known in the art as a rule. For example, a method described in Remington's Pharmaceutical Sciences (Merck Publishing Co., Easton, Pa.) may be used.

For example, the injection can be produced by a method routinely used in the art which involves dissolving the drug delivery particle of the first embodiment in a pharmaceutically acceptable solvent and adding, if necessary, a pharmaceutically acceptable carrier to the resulting solution.

Examples of the "pharmaceutically acceptable solvent" include water, ethanol, propylene glycol, ethoxylated isostearyl alcohol, polyoxygenated isostearyl alcohol, and polyoxyethylene sorbitan fatty acid esters. Desirably, such a solvent is sterilized and preferably adjusted, if necessary, to be isotonic to blood.

3-5. Method for Applying Drug Composition

The drug delivery particle serving as an active ingredient in the drug composition is based on target cell-specific viral infection activities. Hence, the drug composition can be applied in a unit form known in the art by any method capable of contacting the drug delivery particle contained in the drug composition with its target cell.

When the recipient organism is an animal, examples of dosage unit forms known in the art include oral and parenteral administration methods as mentioned above. The parenteral administration methods can be further subdivided into local administration methods (e.g., interstitial administration methods such as subcutaneous administration, intramuscular administration, and intravenous administration, percutaneous administration, transmucosal administration, and transrectal administration). The drug composition of the present invention may be used in any of these dosage unit forms. The administration method is preferably, but not limited to, injection, oral administration, or transmucosal administration.

The injection is preferred because this method can administer the drug composition directly to a target site or its neighborhood and can systemically spread the drug delivery particle via blood. In addition, the injection is relatively low invasive and puts only small burdens on a subject. The site to which the drug composition is injected by the injection is not particularly limited. Examples thereof include intravenous, intraarterial, intrahepatic, intramuscular, intraarticular, intramedullary, intraspinal, intraventricular, percutaneous, subcutaneous, intracutaneous, intraperitoneal, intranasal, intrarectal, and sublingual sites. Intravascular injection such as intravenous injection or intraarterial injection is preferred.

The oral administration or the transmucosal administration is preferred because this method is low invasive and simply achieves administration when the drug delivery particle can be incorporated into a body via the intestinal mucosa, the oral mucosa, the pharyngeal mucosa, the rhinal mucosa, or the like.

When the recipient organism is a plant, the drug composition can be applied thereto in a dosage unit form known in the art by any routine method known in the art that is capable of contacting the drug delivery particle contained in the drug composition with a plant body. Examples of the method for contacting the drug delivery particle with a plant body include methods such as nebulization to, spraying to, application to, injection to, dipping of, and wound inoculation (including needle prick inoculation) to the plant body, and absorption from the root. The site in the recipient plant body with which the drug delivery particle is contacted is not particularly limited and can be any desired position such as above-ground parts including leaves, flower buds, fruits, stems, and branches, or underground parts including roots, rhizomes, and tuberous roots. The site can be appropriately determined in consideration of the infection route of the virus from which the drug delivery particle is derived.

EXAMPLES

Example 1: Large-Scale Production of AAV-Derived Empty Capsid—(1)

(Objective)

E1 gene region expression plasmids were further introduced to existing HEK293 cells containing an endogenous E1 gene region. Change in the amount of AAV produced depending on the amount of the plasmids introduced was tested.

(Method)

Sixteen 225-cm$^2$ flasks were used. $2 \times 10^7$ 293 cells per flask were cultured in a 10% FBS$^+$/DMEM/F12 medium at 37° C. under 5% CO$_2$. After culture for 48 hours, 23 µg/flask of AAV vector plasmids containing AAV inverted terminal repeats (ITRs) and a LacZ gene, 23 µg/flask of AAV helper plasmids containing clones of an AAV2 rep gene and an AAV8 cap gene, 23 µg/flask of adenovirus helper plasmids containing clones of an adenovirus-2 E2A gene region, E4orf6 gene, and VA-RNA-encoding gene, and 0, 2.3, 6.9, or 23 µg/flask of E1 gene region expression plasmids (pE1Δ55) were introduced (n=4 each) to the 293 cells by the calcium phosphate method to replicate AAV particles in the cells. In the case of using 0, 2.3, or 6.9 µg of pE1Δ55, the total amounts of the samples were adjusted to the same amounts among the plasmids with control plasmids (pCMV). The E1 gene region expression plasmid pE1Δ55 contained an E1B gene region except for an E1B55k gene. 6 hours later, the medium was replaced with a 10% FBS+/DMEM/F12 medium. 72 hours later, the cells were recovered, and the freezing and thawing of cell pellets were repeated 6 times while the pellets were well mixed each time by vortex operation. After DNase I digestion of remaining plasmids, the copy number (g.c.) of AAV was determined by the Q-PCR method.

In this context, the detailed cell culture and transfection methods were performed on the basis of methods described in Okada T., et al., Methods Enzymol., Vol 346: Gene Therapy Methods (ed. by M. Ian Phillips), 2002, 378-393; Okada T., et al., Methods., 2002, 28: 237-247; and Okada T., et al., Hum. Gene Ther., 2005, 16: 1212-1218.

(Results)

The results are shown in FIG. 1. As is evident from this diagram, the amount of AAV produced was improved in a manner dependent on the amount of expression plasmids introduced when E1 gene region expression plasmids were introduced to HEK293 cells.

Example 2: Large-Scale Production of AAV-Derived Empty Capsid—(2)

(Objective)

293 cells stably expressing an E1 gene region and a Bcl-x$_L$ gene were constructed. The amount of AAV produced was tested by the enhanced expression of the Bcl-x$_L$ gene.

(Method)

First, a 293 cell line stably expressing an E1 gene region and a Bcl-x$_L$ gene was constructed. E1 gene region expression plasmids pE1Δ55, Bcl-x$_L$ gene expression plasmids, and neomycin expression plasmids were introduced at a ratio of 20:20:1 to 293 cells. Ten clones of a neomycin-resistant cell line were isolated and allowed to grow. Of them, a clone having the highest growth rate was selected to prepare an established cell line, which was in turn designated as a "HEK293EB cell line" (in the present specification, also abbreviated to a "293EB cell line").

Twenty eight 225-cm$^2$ flasks were used. $2 \times 10^7$ 293 cells and 293EB cells per flask were separately cultured in a 10% FBS$^+$/DMEM/F12 medium. After culture for 48 hours, 23 µg/flask of AAV vector plasmids containing AAV ITR-LacZ gene, 23 µg/flask of AAV helper plasmids containing clones of an AAV2 rep gene and an AAV8 cap gene, and 23 µg/flask of adenovirus helper plasmids containing clones of adenovirus-2 E2A, E4, and VA-RNA genes were introduced to the 293EB cells by the calcium phosphate method while these plasmids as well as 23 µg/flask of E1 gene expression plasmids pE1Δ55 was introduced to the 293 cells by the calcium phosphate method. 6 hours later, the medium was replaced with a 10% FBS$^+$/DMEM/F12 medium. 72 hours later, the cells of each line were recovered by centrifugation, and the freezing and thawing of cell pellets were repeated 6 times while the pellets were well mixed each time by vortex operation. After DNase I digestion of remaining plasmids, the genomic copy number of each vector was determined by the Q-PCR method.

In this context, the detailed cell culture and transfection methods followed Example 1.

(Results)

Figure 2:
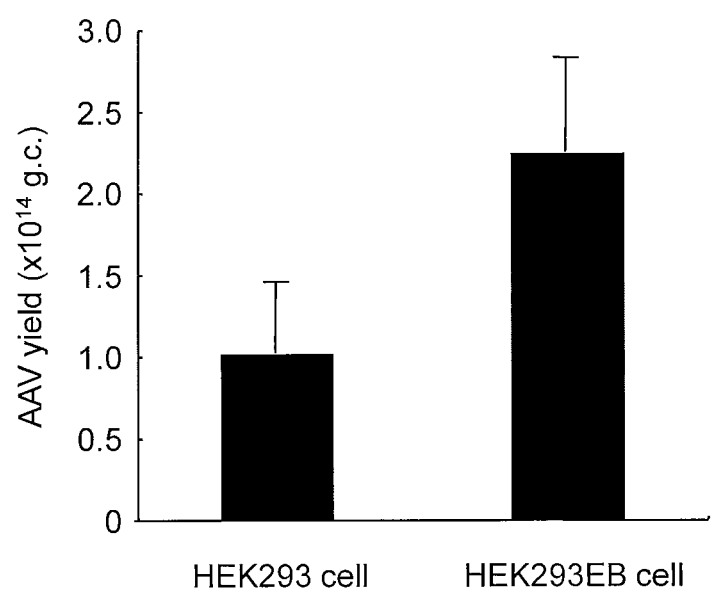
FIG. 2 is a diagram showing results of comparing the amount of AAV produced between HEK293EB cells stably expressing an E1 gene region and a Bcl-$x_L$ gene and normal HEK293 cells.

The results are shown in FIG. 2. As is evident from this diagram, the amount of AAV produced was 2.1 times higher in the 293EB cells stably expressing an E1 gene region and a Bcl-x$_L$ gene than in the 293 cells.

Example 3: Large-Scale Production of AAV-Derived Empty Capsid—(3)

(Objective)

AAV or AAV-derived empty capsids have been purified from a cell homogenate by density-gradient ultracentrifugation or ion-exchange purification in conventional methods. These methods, however, often undergo contamination by impurities and result in insufficient purification efficiency.

The present inventor has found a method for conveniently purifying a virion or an empty capsid, comprising heating the cell homogenate at 55° C. for 30 minutes to coagulate soluble proteins, followed by precipitation and removal. Thus, the following test was conducted for study.

For this purpose, a test was conducted on the optimum conditions under which impurities were efficiently removed from a cell homogenate containing AAV or empty capsids while the early infection activities of AAV or empty capsids were able to be kept as much as possible.

(Method)

$1.4 \times 10^8$ 293 EB cells were cultured in a 10% FBS+/DMEM/F12 medium at 37° C. under 5% $CO_2$ using twenty eight 225-cm² flasks (or one 6320-cm² 10-tier flask). After culture for 48 hours, 650 μg each of AAV vector plasmids containing AAV inverted terminal repeats (ITRs) and a luciferase gene insert, AAV helper plasmids containing clones of AAV2 rep and AAV9 cap genes, and adenovirus helper plasmids containing clones of adenovirus-2 E2A, E4, and VA-RNA genes were introduced to the 293EB cells by the calcium phosphate method to replicate AAV particles and empty AAV capsids in the cells. 6 hours later, the medium was replaced with a 10% FBS+/DMEM/F12 medium. 72 hours later, the cells were recovered by centrifugation, and cell pellets were suspended in 30 mL of a TBS buffer. The freezing and thawing of this sample were repeated 4 to 6 times while the sample was well mixed each time by vortex operation.

150 μL of 1 M $MgCl_2$ and 20 μL of 250 U/μL Benzonase were added to the sample and reacted at 37° C. for 30 minutes. Then, the reaction was stopped by the addition of 300 μL of 0.5 M EDTA. 900 μL of 5 M NaCl was added thereto and well mixed. The mixture was centrifuged at 10,000×g at 4° C. for 10 minutes to recover a supernatant.

The sample thus treated with Benzonase was dispensed in an amount of 1.0 mL/tube to 24 microtubes and untreated or heated under each condition of 50° C. for 30 minutes, 50° C. for 60 minutes, 55° C. for 10 minutes, 55° C. for 20 minutes, or 55° C. for 30 minutes (n=4). The resulting coagulated matter was centrifuged at 4° C. for 10 minutes under a condition of 10,000×g. Precipitates were recovered, and an average amount (mg) thereof was calculated. Also, the capsids treated under each condition described above were mixed in an amount of $1 \times 10^{11}$ genomic copies/well with 293 cells cultured in a 24-well plate. Early infection activities were tested by gene expression in the cells. For the evaluation thereof, luciferase activity was quantified using Bright-Glo Luciferase Assay System (Promega Corp.) and a luminescence plate reader Appliskan manufactured by Thermo Fisher Scientific K.K.

In this context, the detailed cell culture and transfection methods followed Example 1.

(Results)

The results are shown in Table 1. This table indicates luciferase activity by RLU (relative light unit). This result demonstrated that soluble proteins can be removed 30% or more under all of the conditions than the untreated sample. By contrast, treatment at 55° C. for 20 minutes or longer was shown to reduce gene expression. The comparison among the conditions showed that a time of 60 minutes or shorter is appropriate for 50° C. and a time shorter than 20 minutes is appropriate for 55° C.

TABLE 1

| Heating condition | Precipitate (mg) | Average amount of precipitates (mg) | Gene expression (RLU) |
|---|---|---|---|
| Untreated | 25.4 | 25.8 | 166.0 |
| | 25.8 | | |
| | 26.1 | | |
| 50° C./30 minutes | 36.2 | 34.2 | 160.3 |
| | 33.3 | | |
| | 33.0 | | |
| 50° C./60 minutes | 36.9 | 37.5 | 155.0 |
| | 36.7 | | |
| | 39.0 | | |
| 55° C./10 minutes | 34.2 | 33.6 | 143.0 |
| | 32.6 | | |
| | 33.9 | | |
| 55° C./20 minutes | 38.3 | 38.5 | 115.3 |
| | 38.4 | | |
| | 38.9 | | |
| 55° C./30 minutes | 39.5 | 41.7 | 118.3 |
| | 41.8 | | |
| | 43.9 | | |

Example 4: Production of Drug Delivery Particle—(1)

(Objective)

A drug delivery particle was produced by the method for producing a drug delivery particle according to the present invention and tested for the effect of its ability to deliver drugs into cells.

(Method)

(1) Production of Empty Capsid $4 \times 10^8$ 293 EB cells were cultured in a 10% FBS+/DMEM/F12 medium at 37° C. under 5% $CO_2$ using twenty eight 225-cm² flasks (or one 6320-cm² 10-tier flask). After culture for 48 hours, 650 μg each of AAV vector plasmids containing AAV ITRs and an eGFP gene insert, AAV helper plasmids containing clones of AAV9 rep and cap genes, and adenovirus helper plasmids containing clones of adenovirus-2 E2A, E4, and VA-RNA genes were introduced to the 293EB cells by the calcium phosphate method to replicate AAV particles and empty AAV capsids in the cells. 72 hours later, the cells were recovered by centrifugation, and cell pellets were suspended in 30 mL of a TBS buffer. The freezing and thawing of this sample were repeated 4 to 6 times while the sample was well mixed each time by vortex operation.

150 μL of 1 M $MgCl_2$ and 20 μL of 250 U/μL Benzonase were added to the sample and reacted at 37° C. for 30 minutes. Then, the reaction was stopped by the addition of 300 μL of 0.5 M EDTA. 900 μL of 5 M NaCl was added thereto and well mixed. The mixture was centrifuged at 10,000×g at 4° C. for 10 minutes to recover a supernatant.

The sample was then heated at 50° C. for 30 minutes to coagulate soluble proteins. Then, the resulting sample was centrifuged at 10,000×g at 4° C. for 10 minutes to recover a supernatant.

(2) Partial Purification by Ultracentrifugation

A 1.25 g/mL cesium chloride solution was layered over a 1.50 g/mL cesium chloride solution. The supernatant recovered in the step (1) was further layered thereover. After ultracentrifugation at 25,000×g at 16° C. for 3 hours, 0.5 mL each of the cesium chloride layers were recovered from the lower portion of the centrifugation tube. The refractive index (RI) of each fraction was measured. A fraction having RI of 1.365 to 1.368 was recovered and then dialyzed for 30 minutes against an MHN buffer (3.33 mM MES, 3.33 mM HEPES (pH 6.5), 3.33 mM NaOAc) in an amount approximately 100 times that of the sample. The obtained sample was diluted with an MHN buffer in an amount approximately 5 times that of the sample.

(3) Separation and Purification of Empty Capsid

The ion-exchange membrane used was a cation-exchange membrane Mustang S (Pall Corp.) carrying a sulfonic acid group on the surface of a base material. Purification operation was performed using an FPLC system AKTA explorer 100 (GE Healthcare Japan Corp.). Mustang S Acrodisc was equilibrated with an MHN buffer. Then, the sample was applied to the Mustang S Acrodisc at a flow rate of 3 mL/minute so that empty capsids were adsorbed onto the membrane to separate and remove AAV particles. The Mustang S Acrodisc was washed with 10 CV of an MHN buffer. Empty capsids contained in peak fractions were eluted under concentration-gradient conditions of 0 to 100% B (2 M NaCl)/50 CV and recovered in an amount corresponding to 1 mL of a fraction. The obtained capsids were confirmed under electron microscope to be viral genome-free empty capsids having a black portion at the center.

(4) Preparation of Drug Delivery Particle

4 µg of the empty AAV9 capsids prepared in the steps (1) to (3) was mixed with 10 µM (final concentration) 3'-carboxyfluorescein-labeled morpholino oligo (Gene Tools, LLC) (hereinafter, referred to as "fluorescein-PMO") as a drug in the presence of 0.5% (final concentration) Triton X-100 (Wako Pure Chemical Industries, Ltd.). Then, the total amount of the mixture was adjusted to 20 µL with PBS. Then, the mixture was mildly stirred and left standing on ice for 30 minutes.

Subsequently, Triton X-100 and unintroduced fluorescein-PMO were removed using an ultrafiltration membrane Vivaspin 500 (30 kDa MWCO) (GE Healthcare Japan Corp., Cat. #28-9322-35). Specifically, 20 µL of the mixed sample was suspended in 500 µL of a PBS solution and centrifuged at a speed of 15,000 rpm at 4° C. for 10 minutes using Vivaspin 500. This operation was repeated twice, and the amount of the final sample was adjusted to 20 µL with a PBS solution. The drug delivery particle thus obtained is referred to as "AAV9/PMO" for the sake of convenience.

(5) Introduction to Target Cell

AAV9/PMO prepared in the step (4) was mixed with a human rhabdomyosarcoma cell line RD (obtained from Health Science Research Resources Bank, Japan Health Sciences Foundation; JCRB9072) by administration. The cellular uptake and localization of the drug were evaluated. Specifically, $1.0 \times 10^4$ RD cells were mixed with 7 µL of AAV9/PMO and cultured under culture conditions of 5% $CO_2$ and 37° C. The medium used was a DMEM/F12 (1:1) medium containing penicillin (100 IU/mL) and streptomycin (100 µg/mL) and serum with a final concentration set to 10%. Also, a sample in which only fluorescein-PMO was mixed with $1.0 \times 10^4$ RD cells, and a sample in which fluorescein-PMO was introduced in RD cells using a transfection reagent Endo-Porter (Gene Tools, LLC) for PMO of a conventional technique were prepared for controls. In this procedure, the dose of Endo-Porter was set to 0.6 µL per medium in a 100-µL well, and its final concentration was set to 6 µM.

24 hours after the treatment, fluorescence observation was performed using IX70 fluorescence microscope system manufactured by Olympus Corp. to evaluate the uptake and localization of AAV9/PMO in the RD cells. 120 hours after the treatment, the forms of the RD cells were observed.

(Results)

Figure 3:
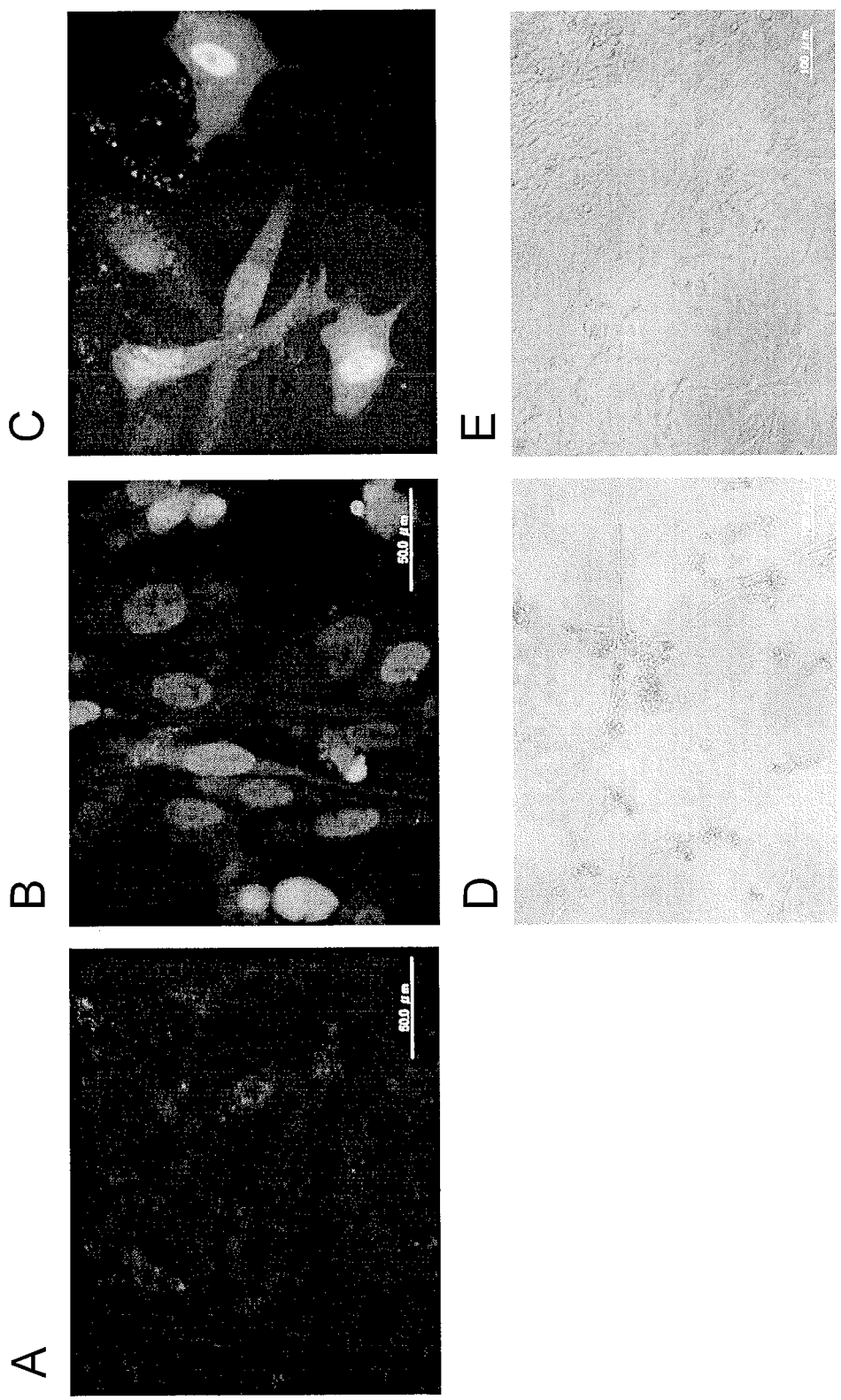
FIG. 3 is a diagram showing the uptake of fluorescently labeled morpholino oligo into a human rhabdomyosarcoma cell line RD.

The results are shown in FIG. 3. FIGS. 3A to 3C are fluorograms taken 24 hours after the administration. FIG. 3A shows the RD cells treated with only fluorescein-PMO. FIG. 3B shows the RD cells treated with Endo-Porter. FIG. 3C shows the RD cells treated with AAV9/PMO. FIGS. 3D and 3E show the forms of the RD cells treated with Endo-Porter and the RD cells treated with AAV9/PMO, respectively, 120 hours after the treatment.

In FIG. 3A, fluorescence was hardly observed, showing that the cells mixed with fluorescein-PMO alone do not take up PMO. By contrast, in FIGS. 3B and 3C, intracellular fluorescence was observed, demonstrating that fluorescein-PMO was successfully taken up by the cells. In FIG. 3C, however, stronger fluorescence than that in FIG. 3B was observed, particularly, in the nuclei, suggesting that PMO was taken up into the cells, particularly, into the nuclei, with high efficiency. Thus, fluorescence intensity in FIGS. 3B and 3C was measured using image analysis software BZ-II (Keyence Corp.) to compare the rate of fluorescein-PMO uptake therebetween. An average value of nuclear fluorescence intensity (RFU) was 55 in the case of using Endo-Porter, whereas the average value was 414 in the case of using AAV9/PMO and was approximately 7.5 times higher for AAV9/PMO than for Endo-Porter. The ratio of nuclear fluorescence intensity to cytoplasmic one was 2.0 in the case of using Endo-Porter, whereas the ratio was 4.6 in the case of using AAV9/PMO and was a little more than 2 times stronger for the empty capsid than for Endo-Porter.

Meanwhile, the RD cells were observed 120 hours after the treatment. As a result, most of the cells in the sample treated with Endo-Porter died (FIG. 3D), suggesting the cytotoxicity of Endo-Porter. By contrast, the treatment with AAV9/PMO hardly killed the cells and did not cause observable morphological change (FIG. 3E).

These results demonstrated that the drug delivery particle of the present invention obtained using the empty capsid, etc. has higher efficiency of PMO delivery into the cells, particularly, into the nuclei, than that of Endo-Porter and further has safety in target cells.

Example 5: Production of Drug Delivery Particle—(2)

(Objective)

In Example 4, 3'-carboxyfluorescein-labeled nucleic acid analog morpholino oligo which is a low-molecular-weight compound was used as a drug to be introduced into the empty capsid, etc., and introduced thereinto by the production method of the present invention. Thus, in this Example, a test was conducted on whether the production method of the present invention can introduce the drug into the empty capsid, etc. as in Example 4 and whether the produced drug delivery particle can be introduced into cells even if the drug was changed to a different nucleic acid or to peptides.

(Method)

(1) Production to Separation and Purification of Empty Capsid

The procedures from the production to separation and purification of empty AAV capsids were performed in the same way as in Example 4, so that the description thereof is omitted here.

(2) Preparation of Drug (i) FITC-siRNA

FITC-labeled siRNA (FITC-siRNA) was used as the different nucleic acid other than morpholino oligo. The FITC-siRNA used was an siRNA consisting of: an siRNA control sequence sense strand siCont-s (Sigma Genosys) labeled 5'-terminally with FITC (5'-Fluorescein (5,6-FAM) UUCUCCGAACGUCACGUUU-3; SEQ ID NO: 8); and an siRNA control sequence antisense strand siCont-as (Sigma Genosys) having the nucleotide sequence represented by 5'-ACGUGACACGUUCGGAGAAUU-3' (SEQ ID NO: 9). The synthesis of the FITC-siRNA was entrusted to Sigma Genosys.

(ii) Alexa 488-BSA and Alexa-IgG

The peptides used were Alexa 488-labeled bovine serum albumin (BSA) (Alexa 488-BSA; Molecular Probes (Life Technologies Inc.); A13100) and anti-rat Alexa-IgG (Molecular Probes (Life Technologies Inc.); A21208).

(3) Preparation of Drug Delivery Particle 7.8 µg/12 µL (0.65 mg/mL) of the empty AAV capsids was mixed with 4 µL of PBS, and 1 µL of 0.5% Pluronic F-68 (nonionic polymer surfactant composed of a PEG copolymer) was added thereto as a surfactant. To the resulting solution, 3 µL of 100 µM FITC-siRNA, 1 µL, of 50 µM Alexa 488-BSA, or 13 µM Alexa-IgG was added, and the mixture was brought up to 20 µL with PBS and left standing at room temperature for 30 minutes. Then, the solution was brought up to 200 µL with PBS and then concentrated to 30 µL, using an ultrafiltration column sterilized with 70% ethanol. This operation was further repeated to remove free siRNA, BSA or IgG.

(4) Introduction to Target Cell

A basic method was the same as the method described in Example 4. A human rhabdomyosarcoma cell line RD (obtained from Health Science Research Resources Bank, Japan Health Sciences Foundation; JCRB9072) cultured in a DMEM/F12 (1:1) medium (Gibco, #11320) supplemented with 10% fetal bovine serum (CCB, Lot 8D0264) and 1% penicillin-streptomycin (Sigma P4458) was inoculated at a concentration of 10,000 cells/well to a 96-well plate and cultured overnight at 37° C. under 5% $CO_2$. Then, a ⅕ amount (6 µL) of the solution concentrated to 30 µL above was added to the culture solution, and the resulting cells were further cultured for 20 hours under the same conditions as above.

After the culture, the culture solution was replaced with PBS(+). Fluorescence observation (excitation: 330-385 nm) was performed using IX70 fluorescence microscope system manufactured by Olympus Corp. to evaluate the uptake and localization of AAV9/PMO in the RD cells.

(Results)

Figure 6:
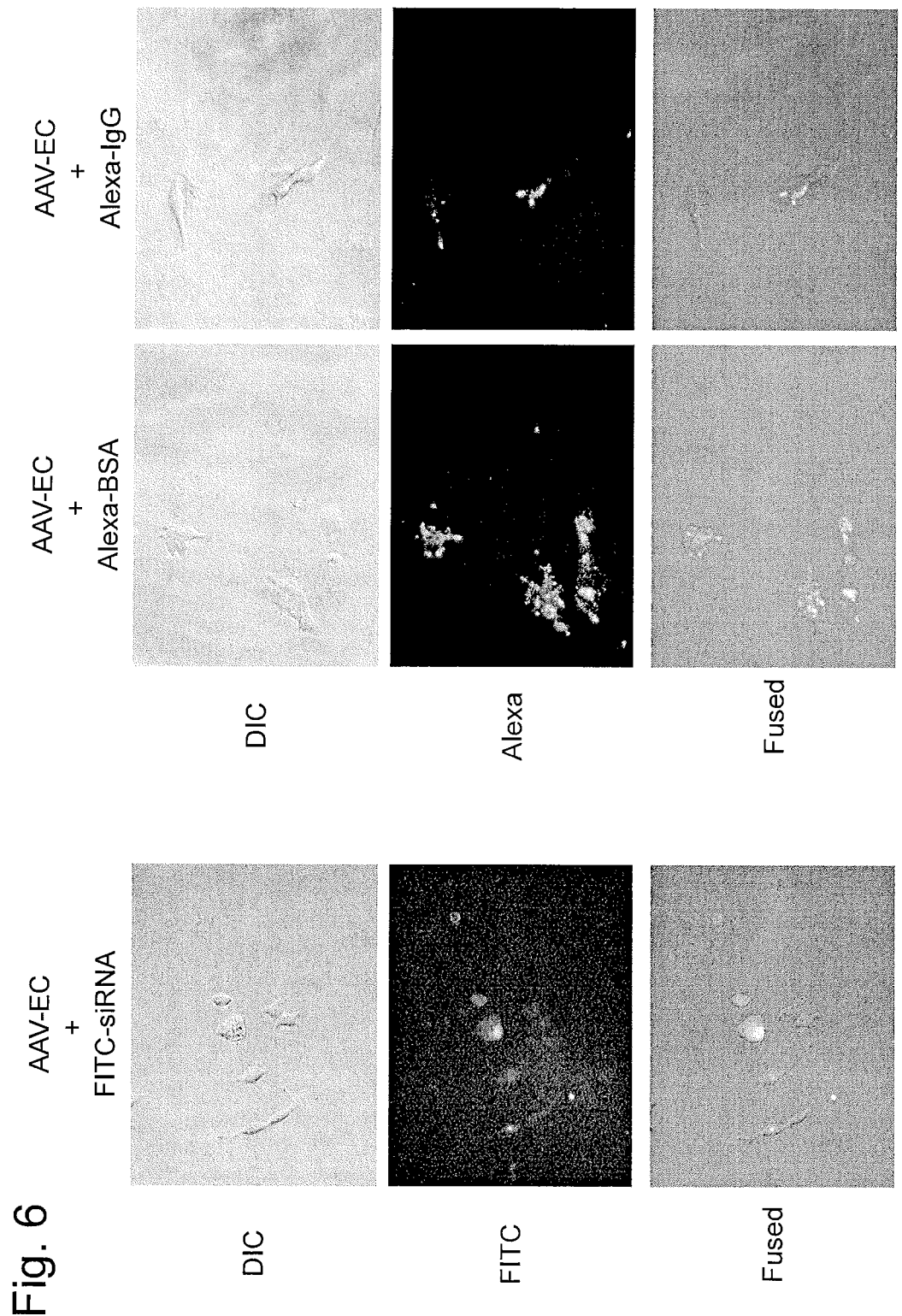
FIG. 6 is a diagram showing the uptake, into a human rhabdomyosarcoma cell line RD, of a drug delivery particle comprising an empty AAV capsid (AAV-EC) and FITC-labeled siRNA, Alexa-labeled BSA, or Alexa-labeled IgG treated by the method of the present invention. In each column, the uppermost image shows RD cells under differential interference microscope (DIC). The middle image shows fluorescence from FITC or Alexa. The lowermost image shows an image into which these two images were fused using image software (Olympus DP Manager version 3.1.1.208).

The results are shown in FIG. 6. This result demonstrated that the production method of the present invention can introduce, into the empty capsid, etc., even a nucleic acid (FITC-labeled siRNA) other than morpholino oligo and even Alexa-labeled peptides (BSA and IgG) and the drug delivery particle can be introduced into cells. Particularly, the introduced FITC-siRNA was also shown to be delivered into nuclei.

These results demonstrated that the production method of the present invention is capable of introducing a nucleic acid, a peptide, a low-molecular-weight compound, and a combination thereof into an empty capsid, etc. and the resulting drug delivery particle is introduced into a predetermined cell on the basis of the infectivity of the viral capsid, etc.

Example 6: Effect of Concentration of Surfactant (Objective)

A test was conducted on the concentration conditions of a surfactant for efficiently introducing a drug into an empty capsid, etc.

(Method)

The basic procedures for preparing the drug delivery particle followed the method described above in Example 4(4) except that: the surfactant used was Tween 20 and its concentration was set to 0, 0.5, 0.75, 1, 3, and 10%; the drug used was FITC-labeled PMO (hereinafter, referred to as "FITC-PMO"); and empty AAV capsids and Tween 20 were mixed and then left standing at 4° C. for 30 minutes.

Empty capsids containing introduced FITC-PMO, i.e., drug delivery particles, were separated from unintroduced free FITC-PMO by centrifugation using an ultrafiltration membrane Vivaspin 500 (30 kDa MWCO). Then, the fluorescence intensity of each sample was measured, and its ratio to the amount of fluorescence before application to the column was calculated and defined as an uptake rate.

(Results)

Figure 4:
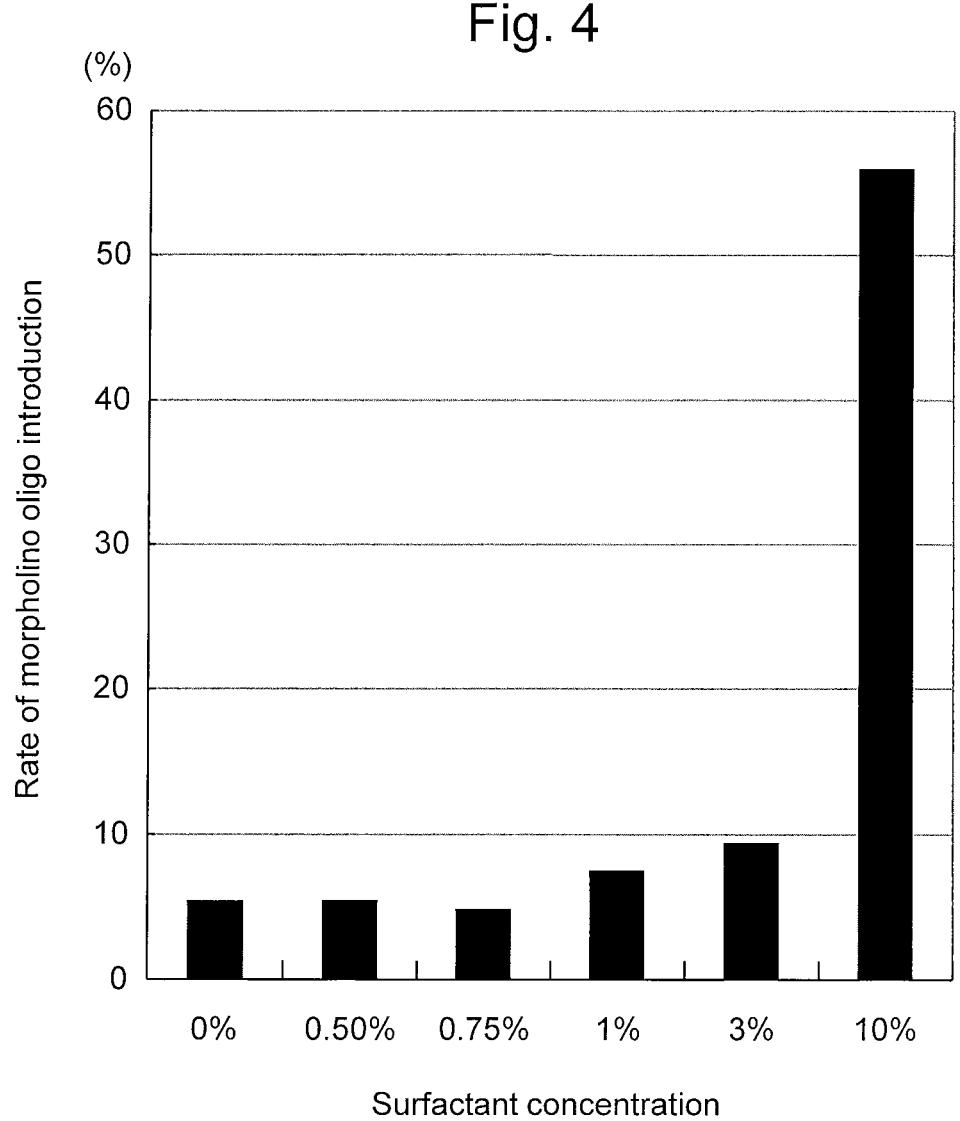
FIG. 4 is a diagram showing the effect of the concentration of a surfactant on the introduction of fluorescently labeled morpholino oligo into an empty AAV capsid.

The results are shown in FIG. 4. The uptake rate rose in a concentration-dependent manner, demonstrating that uptake as effective as the uptake of more than half of the drug delivery particles can be achieved at a surfactant concentration of 10%.

Example 7: Cell-Specific Delivery Activity of Empty Capsid (Objective)

The empty capsid, etc. used in the drug delivery particle of the present invention was tested for its target cell-specific delivery activity.

(Method)

AAV9-derived empty capsids were fluorescently labeled using Alexa Fluor 568 Protein Labeling Kit (Molecular Probes (Life Technologies Inc.)). A specific labeling method followed the protocol included therein. Subsequently, a human fibroblast line WI-38 was infected by MyoD expression adenovirus vectors (MOI=10). The fluorescently labeled empty AAV9 capsids were administered to the cells thus treated to induce muscle differentiation or to untreated cells. 4 days after the infection by MyoD expression adenovirus vectors and 16 hours after the empty AAV9 capsid administration, fluorescence was observed in the cells. In this context, the target cell of AAV9 is a muscle cell.

(Results)

The results are shown in FIG. 5. FIG. 5A shows the untreated WI-38 line. FIG. 5B shows the WI-38 line treated to induce muscle differentiation. Only slight fluorescence was observed in the undifferentiated WI-38 cells (FIG. 5A), whereas strong fluorescence was observed in the cytoplasms or peri-nuclear membrane areas of the WI-38 cells differentiated into muscle (FIG. 5B). Specifically, the fluorescently labeled empty AAV9 capsids were confirmed to have high affinity for cells differentiated into muscle and accumulate in the peri-nuclear membrane areas in the cells. This result shows that the empty capsid, etc. has a target cell-specific delivery activity.

All publications, patents, and patent applications cited herein are incorporated herein by reference in their entirety.

The invention claimed is:

1. A method for producing a HEK293 cell line having the enhanced ability to produce adeno-associated virus, comprising a step of simultaneously introducing to a HEK293 cell already endogenously expressing E1A and E1B19k genes:
   an additional E1A gene,
   an additional E1B19k gene,
   an E2A gene,
   an E4orf6 gene, and
   a VA RNA-encoding gene derived from adenovirus,
   thereby producing the HEK293 cell line having the enhanced ability to produce adeno-associated virus, wherein the enhancement is at least 1.6 fold as compared to the HEK293 cell line without introducing the E1A gene and the E1B19k gene.

2. The method according to claim 1, further comprising the steps of:
   introducing a human-derived Bcl-$x_L$ gene to the HEK293 cell line; and
   selecting a HEK293 cell line stably expressing the introduced Bcl-$x_L$ gene.

3. The method according to claim 1, further comprising the steps of:
   introducing a human-derived Bcl-$x_L$ gene to the HEK293 cell line; and
   selecting a HEK293 cell line stably expressing the introduced Bcl-$x_L$ gene;
   wherein the produced HEK293 cell line having the enhanced ability to produce adeno-associated virus expresses all of the introduced genes.

4. A method for producing a HEK293EB cell having the enhanced ability to produce adeno-associated virus, comprising:
   a first step of introducing to a HEK293 cell already endogenously expressing E1A and E1B19k genes a plasmid expressing an E1 coding region comprising an additional E1A gene and an additional E1B19k gene, and Bcl-$x_L$ gene, thereby producing a HEK293EB cell stably expressing the E1 coding region and Bcl-$x_L$ gene;
   a second step of isolating the HEK293EB cell;
   a third step of introducing to the HEK293EB cell an E2A gene, an E4orf6 gene, and a VA RNA-encoding gene derived from adenovirus,
thereby producing the HEK293EB cell having the enhanced ability to produce adeno-associated virus, wherein the enhancement is at least 1.6 fold as compared to the HEK293 cell without introducing the additional E1A gene and the E1B19k gene.

* * * * *

SEQUENCE LISTING

<160> NUMBER OF SEQ ID NOS: 9

<210> SEQ ID NO 1
<211> LENGTH: 2211
<212> TYPE: DNA
<213> ORGANISM: Adeno-Associated Virus 1

<400> SEQUENCE: 1

| | | | | | |
|---|---|---|---|---|---|
| atggctgccg | atggttatct | tccagattgg | ctcgaggaca | acctctctga | gggcattcgc | 60 |
| gagtggtggg | acttgaaacc | tggagccccg | aagcccaaag | ccaaccagca | aaagcaggac | 120 |
| gacggccggg | gtctggtgct | tcctggctac | aagtacctcg | acccttcaa | cggactcgac | 180 |
| aaggggagc | ccgtcaacgc | ggcggacgca | gcggccctcg | agcacgacaa | ggcctacgac | 240 |
| cagcagctca | aagcgggtga | caatccgtac | ctgcggtata | accacgccga | cgccgagttt | 300 |
| caggagcgtc | tgcaagaaga | tacgtctttt | gggggcaacc | tcgggcgagc | agtcttccag | 360 |
| gccaagaagc | gggttctcga | acctctcggt | ctggttgagg | aaggcgctaa | gacggctcct | 420 |
| ggaaagaaac | gtccggtaga | gcagtcgcca | caagagccag | actcctcctc | gggcatcggc | 480 |
| aagacaggcc | agcagcccgc | taaaaagaga | ctcaattttg | gtcagactgg | cgactcagag | 540 |
| tcagtccccg | atccacaacc | tctcggagaa | cctccagcaa | ccccgctgc | tgtgggacct | 600 |
| actacaatgg | cttcaggcgg | tggcgcacca | atggcagaca | taacgaagg | cgccgacgga | 660 |
| gtgggtaatg | cctcaggaaa | ttggcattgc | gattccacat | ggctgggcga | cagagtcatc | 720 |
| accaccagca | cccgcacctg | gcccttgccc | acctacaata | accacctcta | caagcaaatc | 780 |
| tccagtgctt | caacggggc | cagcaacgac | aaccactact | tcggctacag | cacccccctgg | 840 |
| gggtattttg | atttcaacag | attccactgc | cacttttcac | cacgtgactg | gcagcgactc | 900 |
| atcaacaaca | attggggatt | ccggcccaag | agactcaact | tcaaactctt | caacatccaa | 960 |
| gtcaaggagg | tcacgacgaa | tgatggcgtc | acaaccatcg | ctaataacct | taccagcacg | 1020 |
| gttcaagtct | tctcggactc | ggagtaccag | cttccgtacg | tcctcggctc | tgcgcaccag | 1080 |
| ggctgcctcc | ctccgttccc | ggcggacgtg | ttcatgattc | cgcaatacgg | ctacctgacg | 1140 |
| ctcaacaatg | gcagccaagc | cgtgggacgt | tcatccttt | actgcctgga | atatttccct | 1200 |
| tctcagatgc | tgagaacggg | caacaacttt | accttcagct | acaccttga | ggaagtgcct | 1260 |
| ttccacagca | gctacgcgca | cagccagagc | ctggaccggc | tgatgaatcc | tctcatcgac | 1320 |
| caatacctgt | attacctgaa | cagaactcaa | aatcagtccg | gaagtgccca | aaacaaggac | 1380 |
| ttgctgttta | gccgtgggtc | tccagctggc | atgtctgttc | agcccaaaaa | ctggctacct | 1440 |
| ggaccctgtt | atcggcagca | gcgcgtttct | aaaacaaaaa | cagacaacaa | caacagcaat | 1500 |
| tttacctgga | ctggtgcttc | aaaatataac | ctcaatgggc | gtgaatccat | catcaaccct | 1560 |
| ggcactgcta | tggcctcaca | caaagacgac | gaagacaagt | tctttcccat | gagcggtgtc | 1620 |
| atgatttttg | gaaaagagag | cgccggagct | tcaaacactg | cattggacaa | tgtcatgatt | 1680 |
| acagacgaag | aggaaattaa | agccactaac | cctgtggcca | ccgaaagatt | tgggaccgtg | 1740 |
| gcagtcaatt | tccagagcag | cagcacagac | cctgcgaccg | gagatgtgca | tgctatggga | 1800 |
| gcattacctg | gcatggtgtg | gcaagataga | gacgtgtacc | tgcagggtcc | catttgggcc | 1860 |
| aaaattcctc | acacagatgg | acactttcac | ccgtctcctc | ttatgggcgg | ctttggactc | 1920 |
| aagaacccgc | ctcctcagat | cctcatcaaa | aacacgcctg | ttcctgcgaa | tcctccggcg | 1980 |
| gagttttcag | ctcaaagtt | tgcttcattc | atcacccaat | actccacagg | acaagtgagt | 2040 |
| gtggaaattg | aatgggagct | gcagaaagaa | aacagcaagc | gctggaatcc | cgaagtgcag | 2100 |

| | |
|---|---|
| tacacatcca attatgcaaa atctgccaac gttgatttta ctgtggacaa caatggactt | 2160 |
| tatactgagc ctcgcccat tggcacccgt taccttaccc gtcccctgta a | 2211 |

<210> SEQ ID NO 2
<211> LENGTH: 2208
<212> TYPE: DNA
<213> ORGANISM: Adeno-Associated Virus 2

<400> SEQUENCE: 2

| | |
|---|---|
| atggctgccg atggttatct tccagattgg ctcgaggaca ctctctctga aggaataaga | 60 |
| cagtggtgga agctcaaacc tggcccacca ccaccaaagc ccgcagagcg gcataaggac | 120 |
| gacagcaggg gtcttgtgct tcctgggtac aagtacctcg gacccttcaa cggactcgac | 180 |
| aagggagagc cggtcaacga ggcagacgcc gcggccctcg agcacgacaa agcctacgac | 240 |
| cggcagctcg acagcggaga caacccgtac ctcaagtaca accacgccga cgcggagttt | 300 |
| caggagcgcc ttaaagaaga tacgtctttt gggggcaacc tcggacgagc agtcttccag | 360 |
| gcgaaaaaga gggttcttga acctctgggc ctggttgagg aacctgttaa gacggctccg | 420 |
| ggaaaaaaga ggccggtaga gcactctcct gtggagccag actcctcctc gggaaccgga | 480 |
| aaggcgggcc agcagcctgc aagaaaaaga ttgaattttg gtcagactgg agacgcagac | 540 |
| tcagtacctg accccagcc tctcggacag ccaccagcag cccctctgg tctgggaact | 600 |
| aatacgatgg ctacaggcag tggcgcacca atggcagaca taacgaggg cgccgacgga | 660 |
| gtgggtaatt cctcgggaaa ttggcattgc gattccacat ggatgggcga cagagtcatc | 720 |
| accaccagca cccgaacctg gcccctgccc acctacaaca accacctcta caaacaaatt | 780 |
| tccagccaat caggagcctc gaacgacaat cactactttg ctacagcac ccttgggg | 840 |
| tattttgact tcaacagatt ccactgccac tttcaccac gtgactggca agactcatc | 900 |
| aacaacaact ggggattccg acccaagaga ctcaacttca gctctttaa cattcaagtc | 960 |
| aaagaggtca cgcagaatga cggtacgacg acgattgcca ataaccttac cagcacggtt | 1020 |
| caggtgttta ctgactcgga gtaccagctc ccgtacgtcc tcggctcggc gcatcaagga | 1080 |
| tgcctcccgc cgttcccagc agacgtcttc atggtgccac agtatggata cctcaccctg | 1140 |
| aacaacggga gtcaggcagt aggacgctct tcatttact gcctggagta ctttccttct | 1200 |
| cagatgctgc gtaccggaaa caactttacc ttcagctaca cttttgagga cgttcctttc | 1260 |
| cacagcagct acgctcacag ccagagtctg gaccgtctca tgaatcctct catcgaccag | 1320 |
| tacctgtatt acttgagcag aacaaacact ccaagtggaa ccaccacgca gtcaaggctt | 1380 |
| cagtttctc aggccggagc gagtgacatt cgggaccagt ctaggaactg gcttcctgga | 1440 |
| ccctgttacc gccagcagcg agtatcaaag acatctgcgg ataacaacaa cagtgaatac | 1500 |
| tcgtggactg gagctaccaa gtaccacctc aatggcagag actctctggt gaatccgggc | 1560 |
| ccggccatgg caagccacaa ggacgatgaa gaaaagtttt tccctcagag cggggttctc | 1620 |
| atctttggga agcaaggctc agagaaaaca aatgtggaca ttgaaaaggt catgattaca | 1680 |
| gacgaagagg aaatcaggac aaccaatccc gtggctacgg agcagtatgg ttctgtatct | 1740 |
| accaacctcc agagaggcaa cagacaagca gctaccgcag atgtcaacac acaaggcgtt | 1800 |
| cttccaggca tggtctggca ggacagagat gtgtaccttc aggggcccat ctgggcaaag | 1860 |
| attccacaca cggacggaca ttttcacccc tctcccctca tgggtggatt cggacttaaa | 1920 |
| caccctcctc cacagattct catcaagaac accccggtac ctgcgaatcc ttcgaccacc | 1980 |

```
ttcagtgcgg caaagtttgc ttccttcatc acacagtact ccacgggaca ggtcagcgtg    2040
gagatcgagt gggagctgca gaaggaaaac agcaaacgct ggaatcccga aattcagtac    2100
acttccaact acaacaagtc tgttaatgtg gactttactg tggacactaa tggcgtgtat    2160
tcagagcctc gccccattgg caccagatac ctgactcgta atctgtaa                 2208

<210> SEQ ID NO 3
<211> LENGTH: 2175
<212> TYPE: DNA
<213> ORGANISM: Adeno-Associated Virus 5

<400> SEQUENCE: 3
atgtcttttg ttgatcaccc tccagattgg ttggaagaag ttggtgaagg tcttcgcgag      60
tttttgggcc ttgaagcggg cccaccgaaa ccaaaaccca atcagcagca tcaagatcaa     120
gcccgtggtc ttgtgctgcc tggttataac tatctcggac ccggaaacgg tctcgatcga     180
ggagagcctg tcaacagggc agacgaggtc gcgcgagagc acgacatctc gtacaacgag     240
cagcttgagg cgggagacaa cccctacctc aagtacaacc acgcggacgc cgagtttcag     300
gagaagctcg ccgacgacac atccttcggg ggaaacctcg gaaaggcagt ctttcaggcc     360
aagaaaaggg ttctcgaacc ttttggcctg gttgagaggt gtgctaagac ggcccctacc     420
ggaaagcgga tagacgacca cttccaaaa agaaagaagg ctcggaccga agaggactcc     480
aagccttcca cctcgtcaga cgccgaagct ggacccagcg atccagcag ctgcaaatc      540 ccagcccaac cagcctcaag tttgggagct gatacaatgt ctgcgggagg tggcggccca     600
ttgggcgaca taaccaagg tgccgatgga gtgggcaatg cctcgggaga ttggcattgc     660
gattccacgt ggatgggga cagagtcgtc accaagtcca cccgaacctg ggtgctgccc     720
agctacaaca accaccagta ccgagagatc aaaagcggct ccgtcgacgg aagcaacgcc     780
aacgcctact ttggatacag caccccctgg gggtactttg actttaaccg cttccacagc     840
cactggagcc cccgagactg gcaaagactc atcaacaact actgggggct tcagaccccgg     900 tccctcagag tcaaaatctt caacattcaa gtcaaagagg tcacggtgca ggactccacc     960
accaccatcg ccaacaacct cacctccacc gtccaagtgt ttacggacga cgactaccag    1020
ctgccctacg tcgtcggcaa cgggaccgag ggatgcctgc cggccttccc tccgcaggtc    1080
tttacgctgc cgcagtacgg ttacgcgacg ctgaaccgcg acaacacaga aaatcccacc    1140
gagaggagca gcttcttctg cctagagtac tttcccagca gatgctgag aacgggcaac    1200 aactttgagt ttacctacaa cttggaggag tgccccttcc actccagctt cgctcccagt    1260
cagaacctgt tcaagctggc caacccgctg gtggaccagt acttgtaccg cttcgtgagc    1320
acaaataaca ctggcggagt ccagttcaac aagaacctgg ccgggagata cgccaacacc    1380
tacaaaaact ggttcccggg gcccatgggc cgaacccagg gctggaacct gggctccggg    1440
gtcaaccgcg ccagtgtcag cgccttcgcc acgaccaata gatgagct cgagggcgcg    1500 agttaccagg tgcccccgca gccgaacggc atgaccaaca acctcagg cagcaacacc    1560 tatgccctgg agaacactat gatcttcaac agccagccgg cgaacccggg caccaccgcc    1620
acgtacctcg agggcaacat gctcatcacc agcgagagcg agacgcagcc ggtgaaccgc    1680
gtggcgtaca acgtcggcgg gcagatggcc accaacaacc agagctccac cactgccccc    1740
gcgaccggca cgtacaacct ccaggaaatc gtgcccggca gcgtgtggat ggagagggac    1800
gtgtacctcc aaggacccat ctgggccaag atcccagaga cggggggcgca cttcaccccc    1860 tctccggcca tggcggatt cggactcaaa cacccaccgc ccatgatgct catcaagaac    1920
```

| | |
|---|---|
| acgcctgtgc ccggaaatat caccagcttc tcggacgtgc ccgtcagcag cttcatcacc | 1980 |
| cagtacagca ccgggcaggt caccgtggag atggagtggg agctcaagaa ggaaaactcc | 2040 |
| aagaggtgga acccagagat ccagtacaca aacaactaca cgaccccca gtttgtggac | 2100 |
| tttgccccgg acagcaccgg ggaatacaga accaccagac tatcggaac ccgataccttt | 2160 |
| acccgacccc tttaa | 2175 |

<210> SEQ ID NO 4
<211> LENGTH: 2211
<212> TYPE: DNA
<213> ORGANISM: Adeno-Associated Virus 6

<400> SEQUENCE: 4

| | |
|---|---|
| atggctgccg atggttatct tccagattgg ctcgaggaca acctctctga gggcattcgc | 60 |
| gagtggtggg acttgaaacc tggagccccg aaacccaaag ccaaccagca aaagcaggac | 120 |
| gacgccggg gtctggtgct tcctggctac aagtacctcg accccttcaa cggactcgac | 180 |
| aaggggagc ccgtcaacgc ggcggatgca gcggccctcg agcacgacaa ggcctacgac | 240 |
| cagcagctca aagcgggtga caatccgtac ctgcggtata accacgccga cgccgagttt | 300 |
| caggagcgtc tgcaagaaga tacgtctttt ggggggcaacc tcgggcgagc agtcttccag | 360 |
| gccaagaaga gggttctcga accttttggt ctggttgagg aaggtgctaa gacggctcct | 420 |
| ggaaagaaac gtccggtaga gcagtcgcca caagagccag actcctcctc gggcattggc | 480 |
| aagacaggcc agcagcccgc taaaaagaga ctcaattttg gtcagactgg cgactcagag | 540 |
| tcagtccccg acccacaacc tctcggagaa cctccagcaa ccccgctgc tgtgggacct | 600 |
| actacaatgg cttcaggcgg tggcgcacca atggcagaca taacgaagg cgccgacgga | 660 |
| gtgggtaatg cctcaggaaa ttggcattgc gattccacat ggctgggcga cagagtcatc | 720 |
| accaccagca cccgaacatg gccttgccc acctataaca accacctcta caagcaaatc | 780 |
| tccagtgctt caacggggc cagcaacgac aaccactact cggctacag cacccctgg | 840 |
| gggtattttg atttcaacag attccactgc catttctcac cacgtgactg gcagcgactc | 900 |
| atcaacaaca ttggggatt ccggcccaag agactcaact tcaagctctt caacatccaa | 960 |
| gtcaaggagg tcacgacgaa tgatggcgtc acgaccatcg ctaataaccct taccagcacg | 1020 |
| gttcaagtct ctcggactc ggagtaccag ttgccgtacg tcctcggctc tgcgcaccag | 1080 |
| ggctgcctcc ctccgttccc ggcggacgtg ttcatgattc cgcagtacgg ctacctaacg | 1140 |
| ctcaacaatg cagccaggc agtgggacgg tcatcctttt actgcctgga atatttccca | 1200 |
| tcgcagatgc tgagaacggg caataacttt accttcagct acaccttcga ggacgtgcct | 1260 |
| ttccacagca gctacgcgca agccagagc ctggaccggc tgatgaatcc tctcatcgac | 1320 |
| cagtacctgt attacctgaa cagaactcag aatcagtccg gaagtgccca aaacaaggac | 1380 |
| ttgctgttta gccgggggtc tccagctggc atgtctgttc agcccaaaaa ctggctacct | 1440 |
| ggaccctgtt accggcagca gcgcgtttct aaaacaaaaa cagacaacaa caacagcaac | 1500 |
| tttacctgga ctggtgcttc aaaatataac cttaatgggc gtgaatctat aatcaacccct | 1560 |
| ggcactgcta tggcctcaca caaagacgac aaagacaagt tctttcccat gagcggtgtc | 1620 |
| atgatttttg gaaaggagag cgccggagct tcaaacactg cattggacaa tgtcatgatc | 1680 |
| acagacgaag aggaaatcaa agccactaac cccgtggcca ccgaaagatt tgggactgtg | 1740 |
| gcagtcaatc tccagagcag cagcacagac cctgcgaccg gagatgtgca tgttatggga | 1800 |

-continued

| | |
|---|---|
| gccttacctg gaatggtgtg gcaagacaga gacgtatacc tgcagggtcc tatttgggcc | 1860 |
| aaaattcctc acacggatgg acactttcac ccgtctcctc tcatgggcgg ctttggactt | 1920 |
| aagcacccgc tcctcagat cctcatcaaa acacgcctg ttcctgcgaa tcctccggca | 1980 |
| gagttttcgg ctacaaagtt tgcttcattc atcacccagt attccacagg acaagtgagc | 2040 |
| gtggagattg aatgggagct gcagaaagaa aacagcaaac gctggaatcc cgaagtgcag | 2100 |
| tatacatcta actatgcaaa atctgccaac gttgatttca ctgtggacaa caatggactt | 2160 |
| tatactgagc ctcgccccat tggcacccgt tacctcaccc gtccctgta a | 2211 |

<210> SEQ ID NO 5
<211> LENGTH: 2214
<212> TYPE: DNA
<213> ORGANISM: Adeno-Associated Virus 7

<400> SEQUENCE: 5

| | |
|---|---|
| atggctgccg atggttatct tccagattgg ctcgaggaca acctctctga gggcattcgc | 60 |
| gagtggtggg acctgaaacc tggagccccg aaacccaaag ccaaccagca aaagcaggac | 120 |
| aacggccggg tctggtgct tcctggctac aagtacctcg acccttcaa cggactcgac | 180 |
| aagggggagc ccgtcaacgc ggcggacgca gcggccctcg agcacgacaa ggcctacgac | 240 |
| cagcagctca aagcgggtga caatccgtac ctgcggtata ccacgccga cgccgagttt | 300 |
| caggagcgtc tgcaagaaga tacgtcattt ggggggcaacc tcgggcgagc agtcttccag | 360 |
| gccaagaagc gggttctcga acctctcggt ctggttgagg aaggcgctaa gacggctcct | 420 |
| gcaaagaaga ccggtagagc cgtcacct cagcgttccc ccgactcctc cacgggcatc | 480 |
| ggcaagaaag ccagcagcc cgccagaaag agactcaatt tcggtcagac tggcgactca | 540 |
| gagtcagtcc ccgaccctca acctctcgga gaacctccag cagcgccctc tagtgtggga | 600 |
| tctggtacag tggctgcagg cggtggcgca ccaatggcag acaataacga aggtgccgac | 660 |
| ggagtgggta tgcctcagg aaattggcat gcgattcca catggctggg cgacagagtc | 720 |
| attaccacca gcacccgaac ctgggccctg cccacctaca acaaccacct ctacaagcaa | 780 |
| atctccagtg aaactgcagg tagtaccaac gacaacacct acttcggcta cagcaccccc | 840 |
| tgggggtatt ttgactttaa cagattccac tgccacttct caccacgtga ctggcagcga | 900 |
| ctcatcaaca acaactgggg attccggccc aagaagctgc ggttcaagct cttcaacatc | 960 |
| caggtcaagg aggtcacgac gaatgacggc gttacgacca tcgctaataa ccttaccagc | 1020 |
| acgattcagg tattctcgga ctcggaatac cagctgccgt acgtcctcgg ctctgcgcac | 1080 |
| cagggctgcc tgcctccgtt cccggcggac gtcttcatga ttcctcagta cggctacctg | 1140 |
| actctcaaca tggcagtca gtctgtggga cgttcctcct tctactgcct ggagtacttc | 1200 |
| ccctctcaga tgctgagaac gggcaacaac tttgagttca gctacagctt cgaggacgtg | 1260 |
| cctttccaca gcagctacgc acacagccag agcctggacc ggctgatgaa tccctcatc | 1320 |
| gaccagtact gtactacct ggccagaaca cagagtaacc caggaggcac agctggcaat | 1380 |
| cgggaactgc agttttacca gggcgggcct tcaactatgg ccgaacaagc caagaattgg | 1440 |
| ttacctggac cttgcttccg gcaacaaaga gtctccaaaa cgctggatca aaacaacaac | 1500 |
| agcaactttg cttggactgg tgccaccaaa tatcacctga acggcagaaa ctcgttggtt | 1560 |
| aatcccggcg tcgccatggc aactcacaag gacgacgagg accgctttt cccatccagc | 1620 |
| ggagtcctga tttttggaaa aactggagca actaacaaaa ctacattgga aaatgtgtta | 1680 |
| atgacaaatg aagaagaaat tcgtcctact aatcctgtag ccacggaaga atacgggata | 1740 |

```
gtcagcagca acttacaagc ggctaatact gcagcccaga cacaagttgt caacaaccag      1800
ggagccttac ctggcatggt ctggcagaac cgggacgtgt acctgcaggg tcccatctgg      1860
gccaagattc ctcacacgga tggcaacttt cacccgtctc ctttgatggg cggctttgga      1920
cttaaacatc cgcctcctca gatcctgatc aagaacactc ccgttccgc  taatcctccg      1980 gaggtgttta ctcctgccaa gtttgcttcg ttcatcacac agtacagcac cggacaagtc      2040
agcgtggaaa tcgagtggga gctgcagaag gaaaacagca gcgctggaa  cccggagatt      2100 cagtacacct ccaactttga aaagcagact ggtgtggact tgccgttga  cagccagggt      2160 gtttactctg agcctcgccc tattggcact cgttacctca cccgtaatct gtaa            2214
```

<210> SEQ ID NO 6
<211> LENGTH: 1908
<212> TYPE: DNA
<213> ORGANISM: Adeno-Associated Virus 8
<220> FEATURE:
<221> NAME/KEY: misc_feature
<222> LOCATION: (1695)..(1695)
<223> OTHER INFORMATION: n is a, c, g, or t

<400> SEQUENCE: 6

```
atggctgccg atggttatct tccagattgg ctcgaggaca acctctctga gggcattcgc        60
gagtggtggg cgctgaaacc tggagccccg aagcccaaag ccaaccagca aaagcaggac       120
gacggccggg gtctggtgct tcctggctac aagtaccctcg gacccttcaa cggactcgac       180 aaggggagc  ccgtcaacgc ggcggacgca gcggccctcg agcacgacaa ggcctacgac       240
cagcagctgc aggcgggtga caatccgtac ctgcggtata accacgccga cgccgagttt       300
caggagcgtc tgcaagaaga tacgtctttt gggggcaacc tcgggcgagc agtcttccag       360
gccaagaagc gggttctcga acctctcggt ctggttgagg aaggcgctaa gacggctcct       420
ggaaagaaga gaccggtaga gccatcaccc cagcgttctc cagactcctc tacgggcatc       480
ggcaagaaag gccaacagcc cgccagaaaa agactcaatt ttggtcagac tggcgactca       540
gagtcagttc cagaccctca acctctcgga aacctccag  cagcgccctc tggtgtggga       600
cctaatacaa tggctgcagg cggtggcgca ccaatggcag acaataacga aggcgccgac       660
ggagtgggta gttcctcggg aaattggcat tgcgattcca catggctggg cgacagagtc       720
atcaccacca gcacccgaac ctgggccctg cccacctaca acaaccacct ctacaagcaa       780
atctccaacg gacatcgggg aggagccacc aacgacaaca cctacttcgg ctacagcacc       840
cccctggggg attttgactt taacagattc cactgccact tttcaccacg tgactggcag       900
cgactcatca caacaactg  gggattccgg cccaagagac tcagcttcaa gctcttcaac       960
atccaggtca aggaggtcac gcagaatgaa ggcaccaaga ccatcgccaa taccctcacc      1020
agcaccatcc aggtgtttac ggactcggag taccagctgc cgtacgttct cggctctgcc      1080
caccagggct gcctgcctcc gttccgggcg acgtgttca  tgattcccca gtacggctac      1140
ctaacactca acaacggtag tcaggccgtg gacgctcct  ccttctactg cctggaatac      1200
tttccttcgc agatgctgag aaccggcaac aacttccagt ttacttacac cttcgaggac      1260
gtgccttttc acagcagcta cgcccacagc cagagcttgg accggctgat gaatcctctg      1320
attgaccagt acctgtacta cttgtctcgg actcaaacaa caggaggcac ggcaaatacg      1380
cagactctgg gcttcagcca aggtgggcct aatacaatgg ccaatcaggc aaagaactgg      1440
ctgccaggac cctgttaccg ccaacaacgc gtctcaacga caaccgggca aaacaacaat      1500
```

```
agcaactttg cctggactgc tgggaccaaa taccatctga atggaagaaa ttcattggct    1560
aatcctggca tcgctatggc aacacacaaa gacgacgagg agcgtttttt tcccagtaac    1620
gggatcctga ttttggcaaa caaaatgctg ccagagacaa tgcggattac agcgatgtca    1680
tgctcaccag cgagnaagaa atcaaaacca ctaaccctgt ggctacagag gaatacggta    1740
tcgtggcaga taacttgcag cagcaaaaca cggctcctca aattggaact gtcaacagcc    1800
agggggcctt acccggtatg gtctggcaga accgggacgt gtacctgcag ggtcccatct    1860
gggccaagat tcctcacacg gacggcaact tccacccgtc tccgctga                 1908

<210> SEQ ID NO 7
<211> LENGTH: 2211
<212> TYPE: DNA
<213> ORGANISM: Adeno-Associated Virus 9

<400> SEQUENCE: 7
atggctgccg atggttatct tccagattgg ctcgaggaca accttagtga aggaattcgc      60
gagtggtggg ctttgaaacc tggagcccct caacccaagg caaatcaaca acatcaagac     120
aacgctcgag gtcttgtgct tccgggttac aaataccttg acccggcaa cggactcgac      180
aagggggagc cggtcaacgc agcagacgcg gcggccctcg agcacgacaa ggcctacgac     240
cagcagctca aggccggaga caaccccgtac ctcaagtaca ccacgccga cgccgagttc     300
caggagcggc tcaaagaaga tacgtctttt gggggcaacc tcgggcgagc agtcttccag     360
gccaaaaaga ggcttcttga acctcttggt ctggttgagg aagcggctaa gacggctcct     420
ggaaagaaga ggcctgtaga gcagtctcct caggaaccgg actcctccgc gggtattggc     480
aaatcgggtg cacagcccgc taaaaagaga ctcaatttcg gtcagactgg cgacacagag     540
tcagtcccag accctcaacc aatcggagaa cctccgcag cccctcagg tgtgggatct      600
cttacaatgg cttcaggtgg tggcgcacca gtggcagaca taacgaagg tgccgatgga     660
gtgggtagtt cctcgggaaa ttggcattgc gattcccaat ggctggggga cagagtcatc    720
accaccagca cccgaacctg ggccctgccc acctacaaca tcacctcta caagcaaatc     780
tccaacagca catctggagg atcttcaaat gacaacgcct acttcggcta cagcaccccc    840
tgggggtatt ttgacttcaa cagattccac tgccacttct caccacgtga ctggcagcga    900
ctcatcaaca caactggggg attccggcct aagcgactca acttcaagct cttcaacatt    960
caggtcaaag aggttacgga caacaatgga gtcaagacca tcgccaataa ccttaccagc    1020
acggtccagg tcttcacgga ctcagactat cagctcccgt acgtgctcgg tcggctcac    1080
gagggctgcc tcccgccgtt cccagcggac gttttcatga ttcctcagta cgggtatctg   1140
acgcttaatg atggaagcca ggccgtgggt cgttcgtcct tttactgcct ggaatatttc   1200
ccgtcgcaaa tgctaagaac gggtaacaac ttccagttca gctacgagtt tgagaacgta   1260
cctttccata gcagctacgc tcacagccaa agcctggacc gactaatgaa tcccactcatc   1320
gaccaatact tgtactatct ctcaaagact attaacggtt ctggacagaa tcaacaaacg   1380
ctaaaattca gtgtggccgg acccagcaac atggctgtcc agggaagaaa ctacatacct   1440
ggacccagct accgacaaca acgtgtctca accactgtga ctcaaaacaa caacagcgaa   1500
tttgcttggc ctggagcttc ttcttgggct ctcaatggac gtaatagctt gatgaatcct   1560
ggacctgcta tggccagcca caaagaagga gaggaccgtt tctttcctt gtctggatct   1620
ttaatttttg gcaaacaagg aactggaaga gacaacgtgg atgcggacaa agtcatgata   1680
accaacgaag aagaaattaa aactactaac ccggtagcaa cggagtccta tggacaagtg   1740
```

```
gccacaaacc accagagtgc ccaagcacag gcgcagaccg gctgggttca aaaccaagga    1800
atacttccgg gtatggtttg gcaggacaga gatgtgtacc tgcaaggacc catttgggcc    1860
aaaattcctc acacggacgg caactttcac ccttctccgc tgatgggagg gtttggaatg    1920
aagcacccgc ctcctcagat cctcatcaaa aacacacctg tacctgcgga tcctccaacg    1980
gccttcaaca aggacaagct gaactctttc atcacccagt attctactgg ccaagtcagc    2040
gtggagatcg agtgggagct gcagaaggaa aacagcaagc gctggaaccc ggagatccag    2100
tacacttcca actattacaa gtctaataat gttgaatttg ctgttaatac tgaaggtgta    2160
tatagtgaac cccgccccat tggcaccaga tacctgactc gtaatctgta a            2211

<210> SEQ ID NO 8
<211> LENGTH: 19
<212> TYPE: RNA
<213> ORGANISM: Artificial
<220> FEATURE:
<223> OTHER INFORMATION: siRNA

<400> SEQUENCE: 8
uucuccgaac gucacguuu                                                  19

<210> SEQ ID NO 9
<211> LENGTH: 21
<212> TYPE: RNA
<213> ORGANISM: Artificial
<220> FEATURE:
<223> OTHER INFORMATION: siRNA

<400> SEQUENCE: 9
acgugacacg uucggagaau u                                               21
```